United States Patent
Tosaki et al.

(10) Patent No.: US 6,551,682 B1
(45) Date of Patent: Apr. 22, 2003

(54) METAL-CONTAINING AZO COMPOUND AND OPTICAL RECORDING MEDIA

(75) Inventors: Yoshihiro Tosaki, Ibaraki (JP); Tomiharu Hosaka, Yawata (JP); Toshiaki Kunieda, Minoo (JP); Masatoshi Taniguchi, Kyoto (JP); Noriko Kobayashi, Kyoto (JP); Tomoyuki Hase, Kyoto (JP)

(73) Assignees: Matsushita Electric Industrial Co., Ltd., Osaka (JP); Yamada Chemical Co., Ltd., Kyoto (JP)

( * ) Notice: Subject to any disclaimer, the term of this patent is extended or adjusted under 35 U.S.C. 154(b) by 0 days.

(21) Appl. No.: 09/936,483
(22) PCT Filed: Mar. 14, 2000
(86) PCT No.: PCT/JP00/01526
§ 371 (c)(1), (2), (4) Date: Sep. 14, 2001
(87) PCT Pub. No.: WO00/55136
PCT Pub. Date: Sep. 21, 2000

(30) Foreign Application Priority Data

Mar. 16, 1999 (JP) .......................................... 11-070187

(51) Int. Cl.⁷ ................................................. B32B 3/02
(52) U.S. Cl. ................ 428/64.1; 428/64.8; 430/270.14; 430/270.16
(58) Field of Search ............................. 428/64.1, 64.4, 428/64.8, 913; 430/270.14, 270.16, 495.1, 945; 369/283, 288

(56) References Cited

U.S. PATENT DOCUMENTS

| | | | |
|---|---|---|---|
| 4,241,355 A | | 12/1980 | Bloom et al. |
| 4,358,527 A | * | 11/1982 | Bailey .......................... 430/223 |
| 4,521,506 A | * | 6/1985 | Stolzenberg ................. 430/241 |
| 5,980,622 A | * | 11/1999 | Byers ....................... 106/31.48 |

FOREIGN PATENT DOCUMENTS

| | | | |
|---|---|---|---|
| EP | 0 188 001 | | 7/1986 |
| EP | 937751 | | 8/1990 |
| EP | 649880 | * | 4/1995 |
| EP | 937751 | * | 8/1999 |
| JP | 56-86795 | | 7/1981 |
| JP | 5-67438 | | 9/1993 |
| JP | 200-62321 | * | 2/2000 |
| JP | 2000-62321 | | 2/2000 |

* cited by examiner

Primary Examiner—Elizabeth Mulvaney
(74) Attorney, Agent, or Firm—Wenderoth, Lind & Ponack, L.L.P.

(57) ABSTRACT

There is provided a metal-containing azo compound suitably used for an recording layer of an optical medium, which is represented by at least one of the following general formulae:

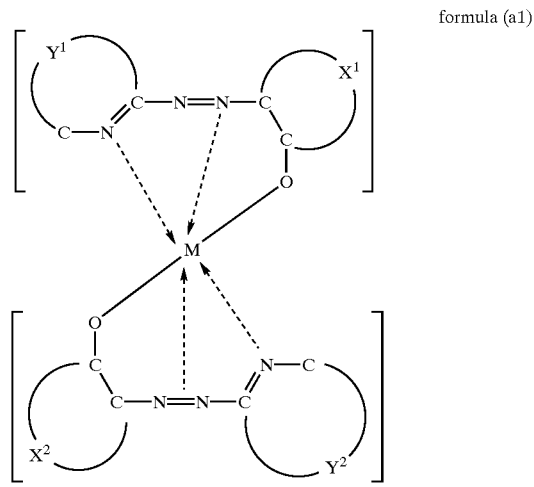

formula (a1)

| | |
|---|---|
| 1 | Substrate |
| 2 | Recording layer |
| 3 | Reflective layer |
| 4 | Adhesive layer |
| 5 | Substrate |
| 6 | Groove |

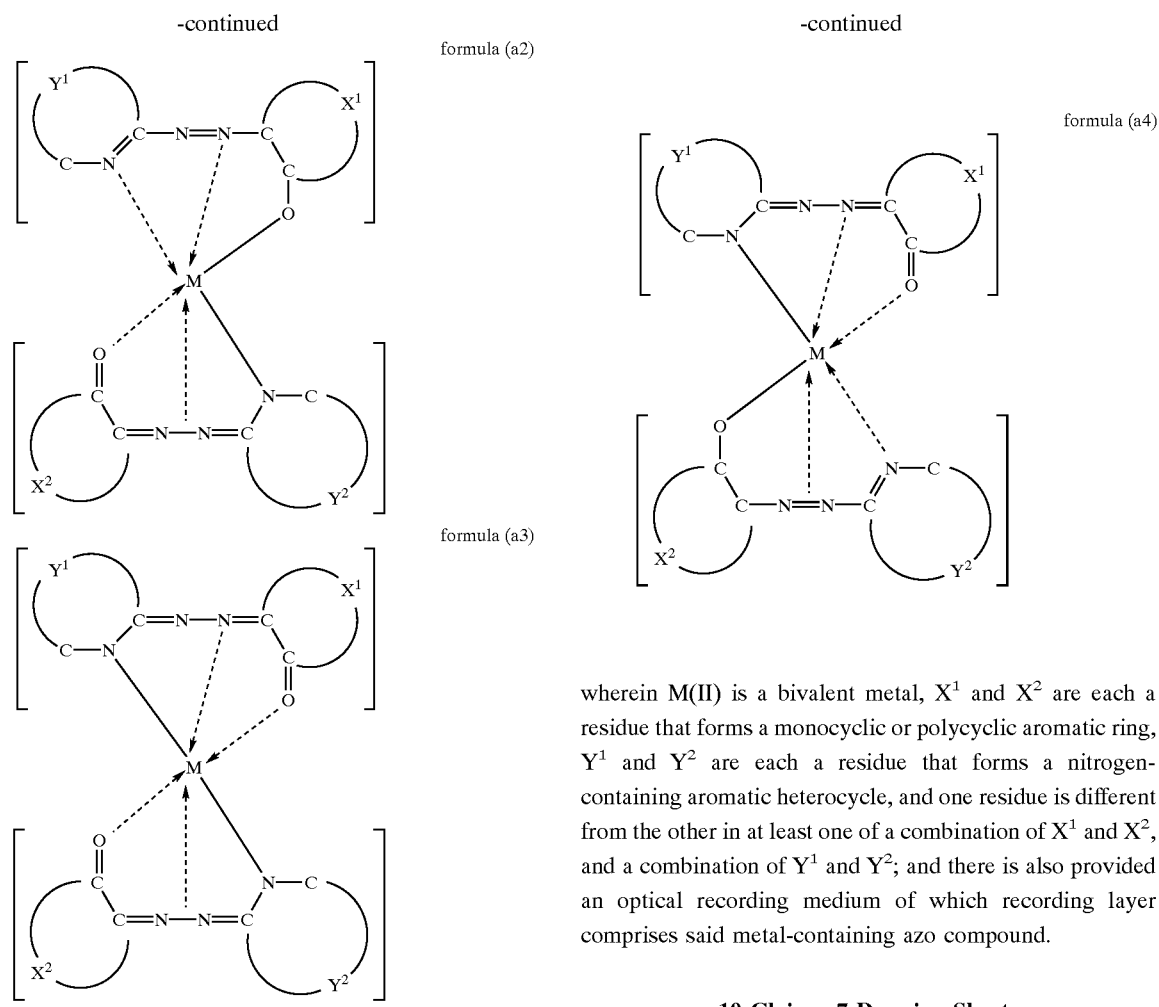

wherein M(II) is a bivalent metal, $X^1$ and $X^2$ are each a residue that forms a monocyclic or polycyclic aromatic ring, $Y^1$ and $Y^2$ are each a residue that forms a nitrogen-containing aromatic heterocycle, and one residue is different from the other in at least one of a combination of $X^1$ and $X^2$, and a combination of $Y^1$ and $Y^2$; and there is also provided an optical recording medium of which recording layer comprises said metal-containing azo compound.

19 Claims, 7 Drawing Sheets

| 1 | Substrate |
| 2 | Recording layer |
| 3 | Reflective layer |
| 4 | Adhesive layer |
| 5 | Substrate |
| 6 | Groove |

METAL-CONTAINING AZO COMPOUND AND OPTICAL RECORDING MEDIA

This application is a 371 application of PCT/JP00/01526, filed Mar. 14, 2000.

TECHNICAL FIELD

The present invention relates to a new metal-containing azo compound and an optical recording medium such as a tape, a disk, or a card for recording information by means of a light beam, particularly an optical recording medium in the form of a disk such as a compact disk (hereafter referred to also as CD) and a digital video disk (hereafter referred to also as DVD), in which the compound is used.

BACKGROUND ART

In recent years, with the spread of CDs, a write-once type optical disk satisfying the CD standard (hereafter referred to also as CD-R) has been developed and used. The CD-R is typically constructed by using a transparent resin substrate having a spiral groove on one surface thereof, applying thereon an organic dyestuff solution (i.e. a solution of an organic dyestuff) by means of a spin coater, then drying the solution to form a recording layer, disposing thereon a reflective layer formed by, for example sputtering gold, and disposing a protective layer formed by applying an ultraviolet-curable resin by means of a spin coater or the like and curing the resin (hereafter, the optical recording medium having the optical absorbing layer formed on the substrate by applying the organic dyestuff solution is referred to as an "application-type" one).

Recordation on the CD-R is performed by forming pits on the recording layer in accordance with information, the pits being formed by changing (for example decomposing) the organic dyestuff and/or by using change of the interference structure of the recording layer due to the change of the organic dyestuff through irradiation of a laser beam having a wavelength of 780 nm from the substrate side to the recording layer. Reproduction of the information recorded on the CD-R is performed by detecting the changes in an amount of light reflected from the pits. In recording information on the CD-R by means of a CD-R writer or the like, servo characteristics which control rotation of a pick-up head along the groove of the substrate are of importance. Therefore, for the CD-R, it is necessary to obtain tracking error signals stably.

The tracking error signals are greatly affected especially by a level difference between recording layer parts on the groove portion and on the inter-groove portion of the substrate. Accordingly, upon producing the above-mentioned application-type CD-R, the following is carried out in order to ensure the tracking error signals. When an organic dyestuff solution is applied for forming a recording layer on a substrate, the solution fills preferentially the groove of the substrate. For this reason, a substrate having a deep groove is utilized to ensure a thickness of the recording layer and tracking error signals. However, as the depth of the groove in the substrate increases, a radial inclination in the groove depth is liable to take place, such as a groove depth decreasing from the inner periphery towards the outer periphery of the substrate, due to the influence of the temperature and the fluidity of the molten resin when forming the substrate. Further, an inclination in the recording layer thickness is liable to take place in the radial direction of the substrate due to a rise in viscosity of the solution caused by evaporation of the solvent during the application of the organic dyestuff solution.

Therefore, an attempt is made to suppress the change of the tracking error signals in the radial direction of the substrate to ensure a necessary level of the tracking error signals by precisely adjusting the application conditions such as a type of the solvent to be used for the organic dyestuff solution, a viscosity of the organic dyestuff solution, rotation control of the spin coater, and surrounding environment condition during the production, and also the drying condition and the like upon forming the recording layer.

Recently, in order to achieve a further higher density of information, a DVD is developed to which a laser having a wavelength around 650 nm is irradiated. The DVD is produced by forming pits with a track pitch of 0.74 μm and the shortest pit length of 0.40 μm on a substrate having a thickness of 0.6 mm by means of a molding apparatus, forming a reflective layer thereon, and further sticking another resin substrate having a thickness of 0.6 mm using an adhesive material such as an ultraviolet-curable resin in order to ensure the hardness of the disk, in the same manner as the CD. Like the CD-R, a writable DVD-R is being developed.

In view of compatibility with the DVD, the DVD-R must include pits which are formed to correspond to the information in a substrate having a narrow groove which has a track pitch of less than or equal to half of that in the CD-R and, in accordance therewith, has a narrower width. In this case, as the track pitch or the groove width of the substrate decreases, the inclination of the groove depth in the radial direction is further increased if the substrate has a deep groove. Accordingly, it is extremely difficult to ensure necessary tracking error signals by the conventionally performed adjustment of the application condition of the organic dyestuff solution and the drying condition.

DISCLOSURE OF INVENTION

In consideration of the above problems, an object of the present invention is to provide a metal-containing azo compound which is suited for a recording layer of an optical recording medium, and to provide an improved write-once type optical recording medium by using the compound which medium ensures more proper tracking error signals to be adapted to high density information recording and has various characteristics depending on the application of the medium, The present invention provides a metal-containing azo compound represented by at least one formula which is selected from the following general formulae (a1), (a2), (a3) and (a4):

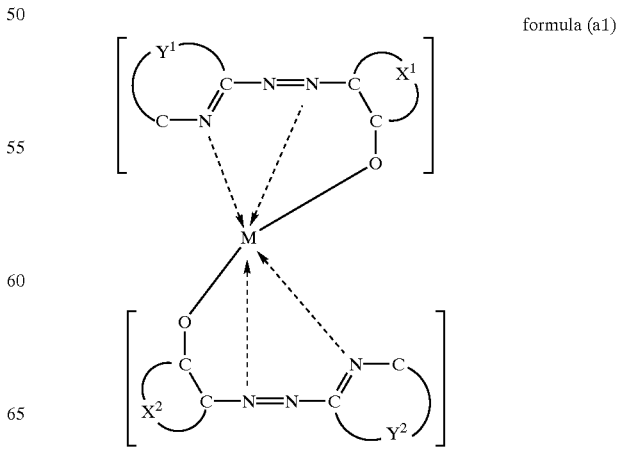

formula (a1)

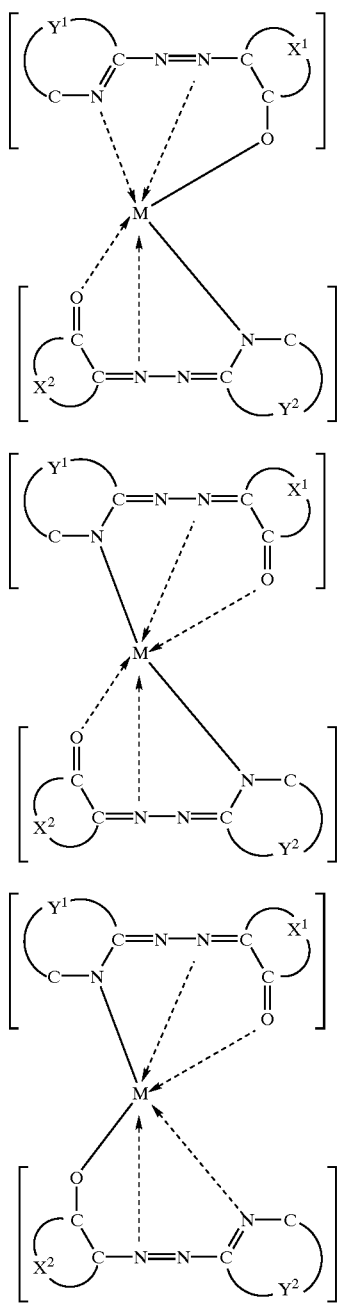

formula (a2)

formula (a3)

formula (a4)

wherein M(II) is a bivalent metal, each of $X^1$ and $X^2$ is a substituted or non-substituted residue that forms a monocyclic or polycyclic aromatic ring together with carbon atoms that are adjacent thereto at its both ends, each of $Y^1$ and $Y^2$ is a substituted or non-substituted residue that forms a nitrogen-containing aromatic heterocycle together with a nitrogen atom and carbon atoms that are adjacent thereto at its both ends, and a substituent when present in the residue is independently selected from the group consisting of a halogen atom, a substituted and non-substituted alkyl group, a substituted and non-substituted alkoxyl group, a substituted and non-substituted alkylthio group, a substituted and non-substituted aryl group, a substituted and non-substituted aryloxyl group, a substituted and non-substituted arylthio group, a nitro group, and a substituted and non-substituted amino group, and one residue is different from the other in at least one of a combination of $X^1$ and $X^2$ and a combination of $Y^1$ and $Y^2$; and the present invention provides an optical recording medium having a recording layer formed on a substrate, the recording layer allowing writing and/or reading information by a laser beam, wherein the recording layer comprises the metal-containing azo compound.

The metal-containing azo compound according to the present invention, which is represented by at least one formula of the above (a1), (a2), (a3) and (a4) is characterized in that two different azo compound ligands are bonded to the bivalent metal. It has been found that when such metal-containing azo compound is contained in a recording layer of an optical recording medium, characteristics brought by both azo compound ligands bonded to the metal appear moderately in the medium, and thus an optical recording medium of which overall performance is improved can be obtained. Hereafter, the present invention is explained in detail.

Figure 1:
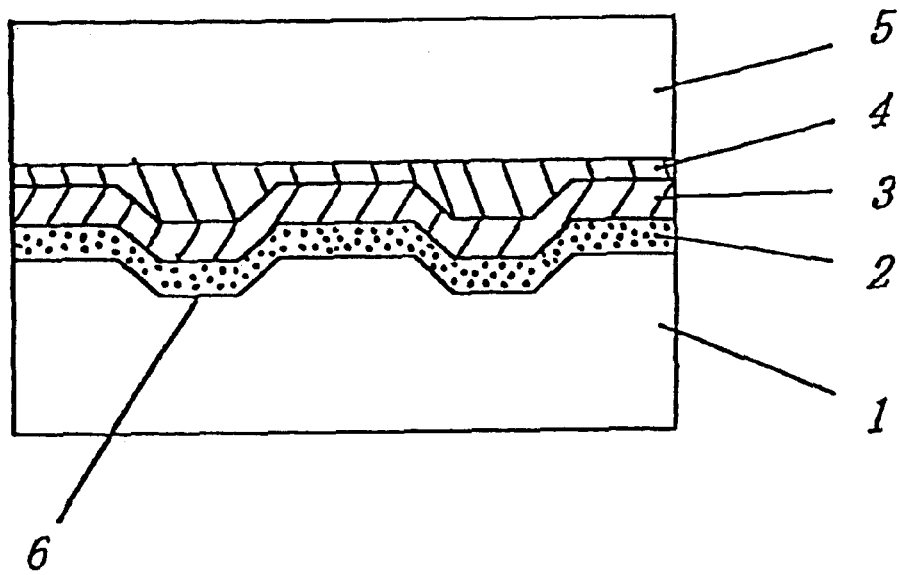
FIG. 1 is an enlarged schematic view illustrating a portion of a cross section of an optical recording medium of the present invention.
Figure 2:
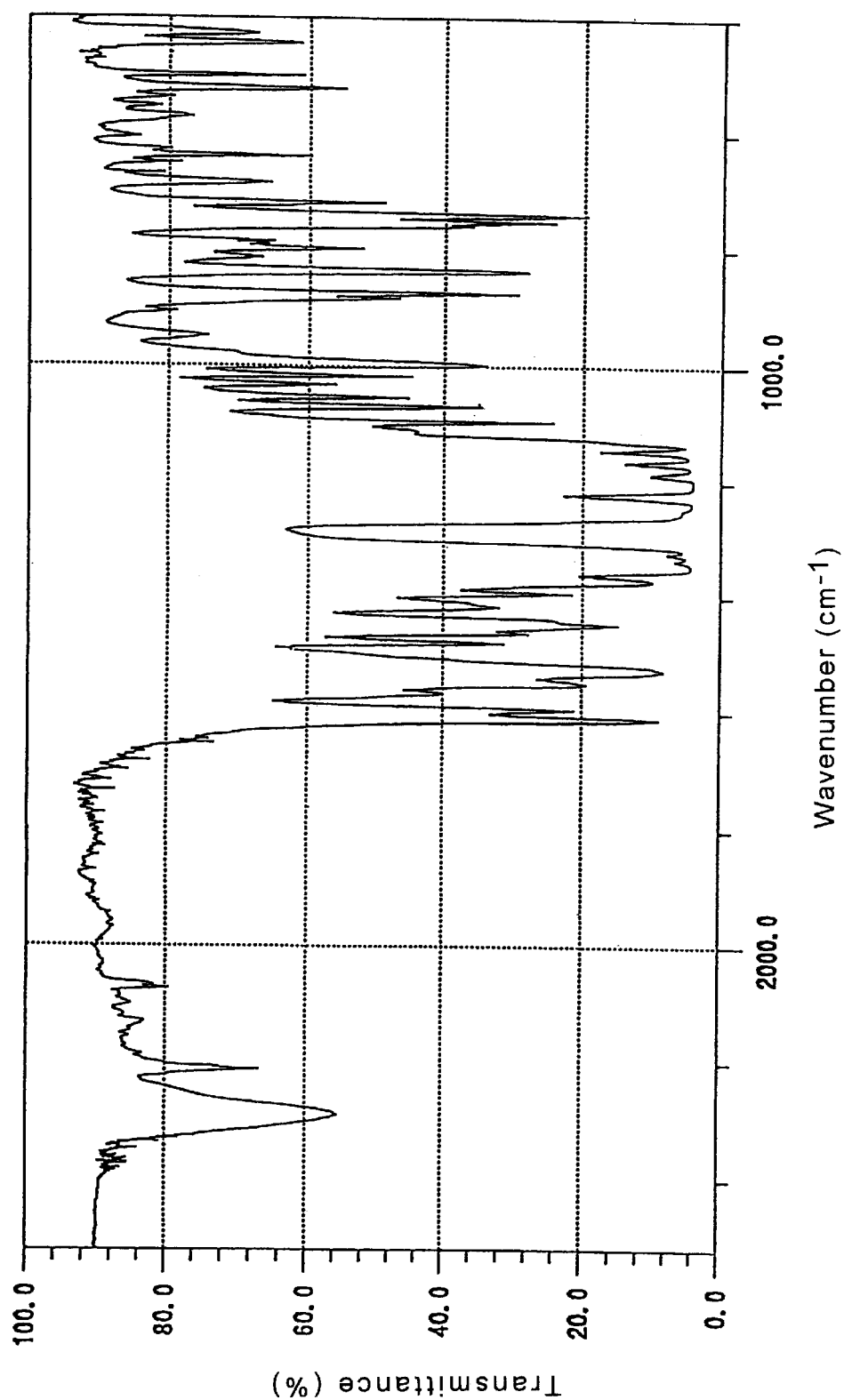
FIG. 2 is a graph illustrating an infrared spectrum of a metal-containing azo compound obtained in Example 4.
Figure 3:
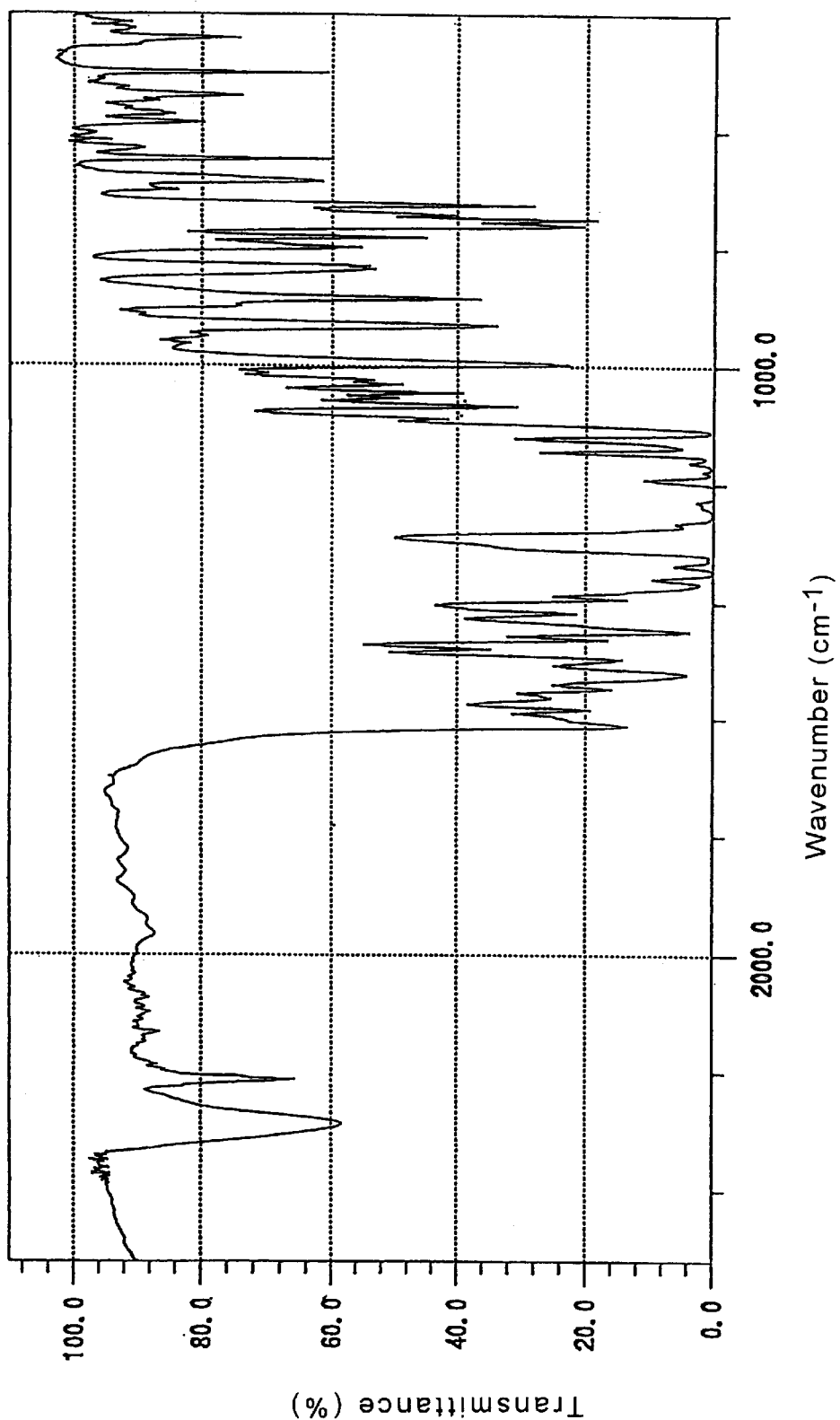
FIG. 3 is a graph illustrating an infrared spectrum of a metal-containing azo compound obtained in Example 15.
Figure 4:
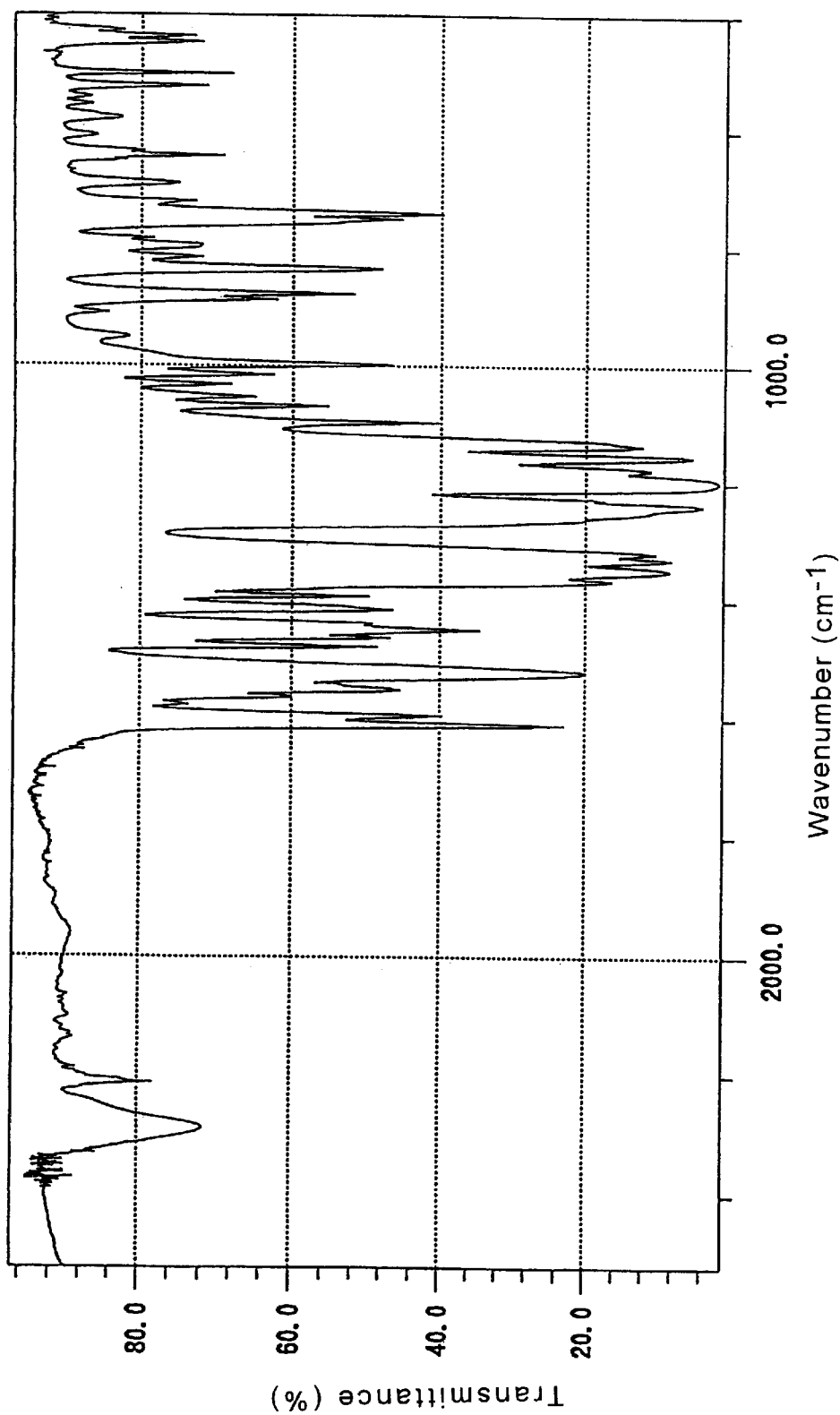
FIG. 4 is a graph illustrating an infrared spectrum of a metal-containing azo compound obtained in Example 17.
Figure 5:
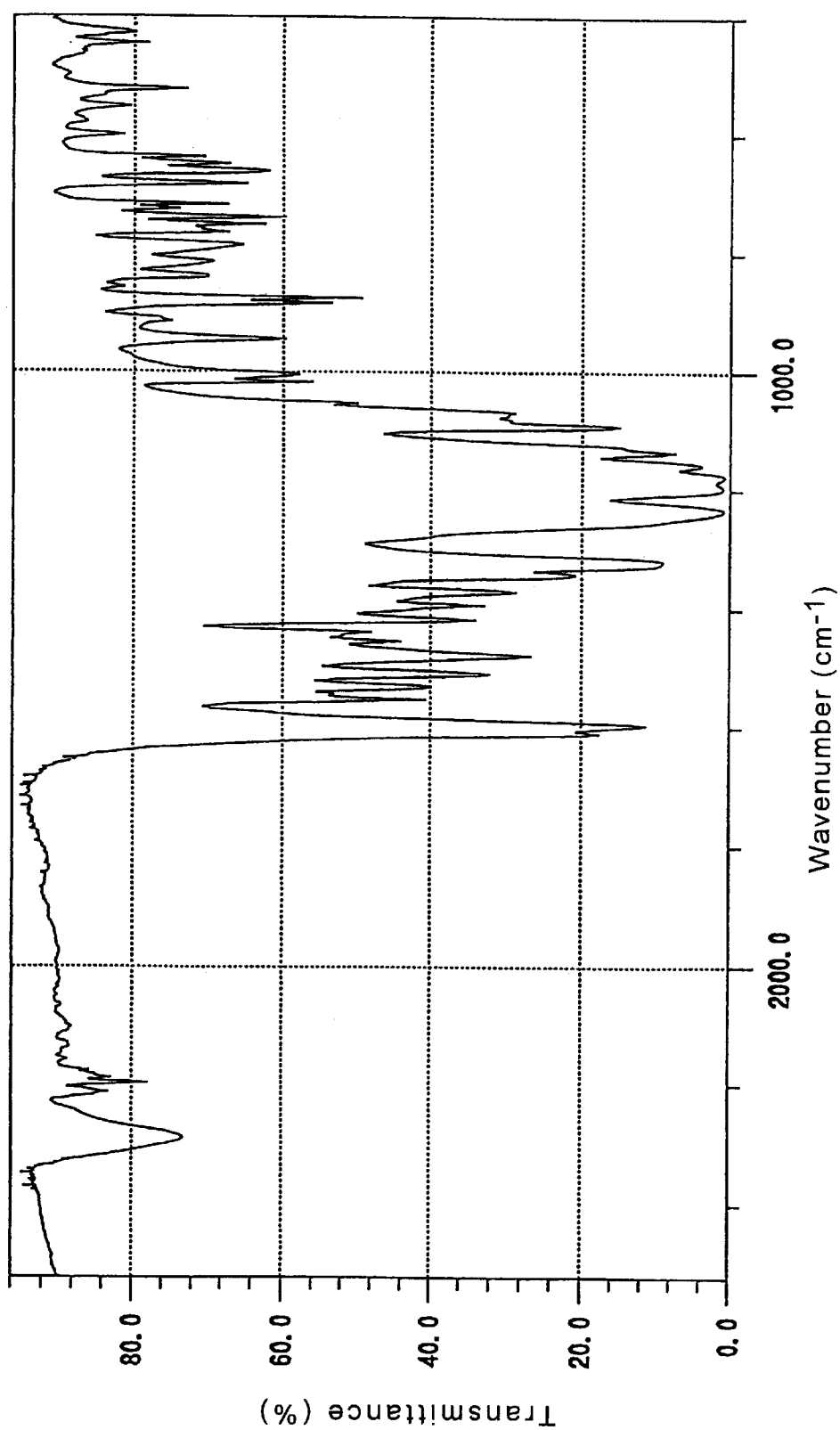
FIG. 5 is a graph illustrating an infrared spectrum of a metal-containing azo compound obtained in Example 19.
Figure 6:
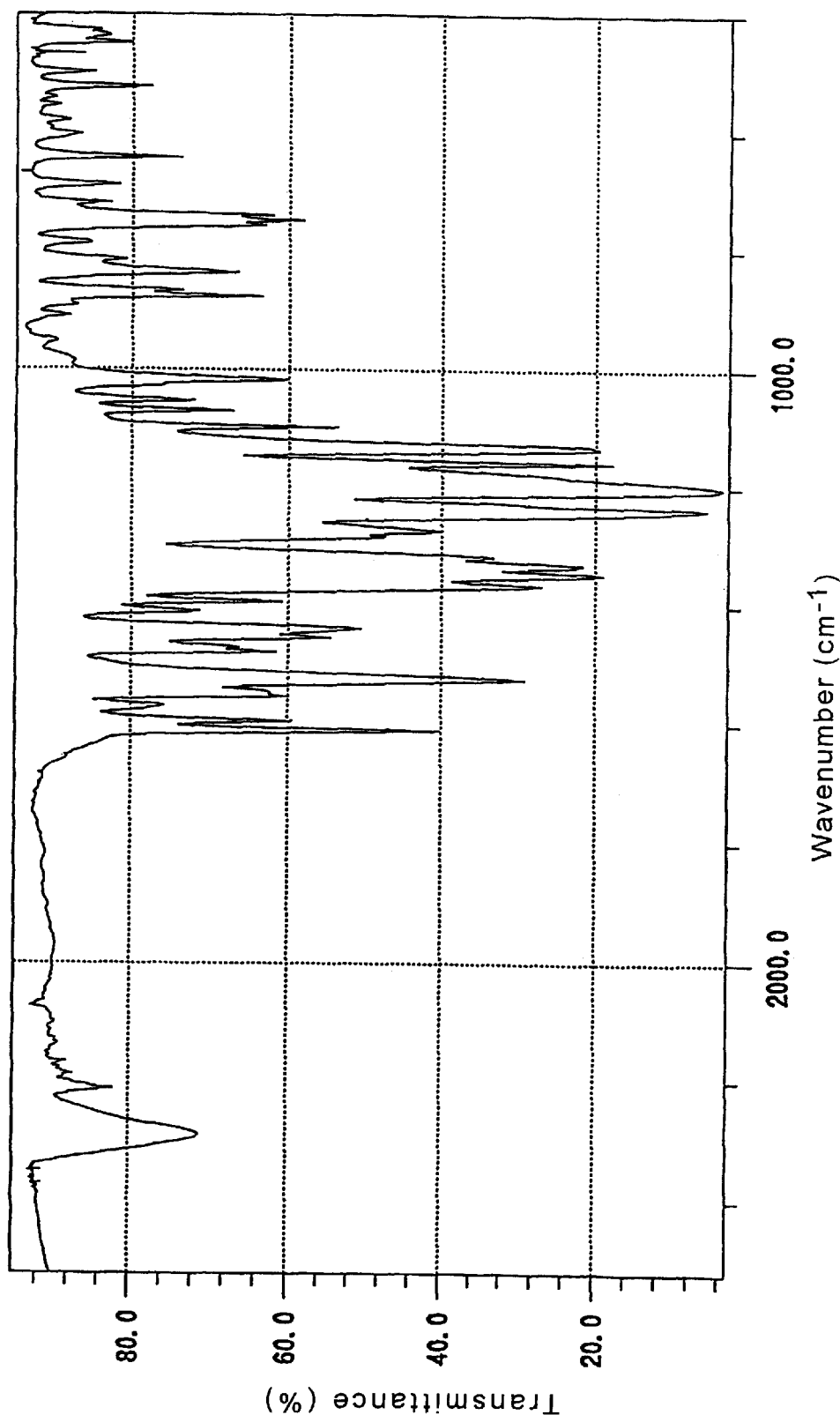
FIG. 6 is a graph illustrating an infrared spectrum of a metal-containing azo compound obtained in Example 22.
Figure 7:
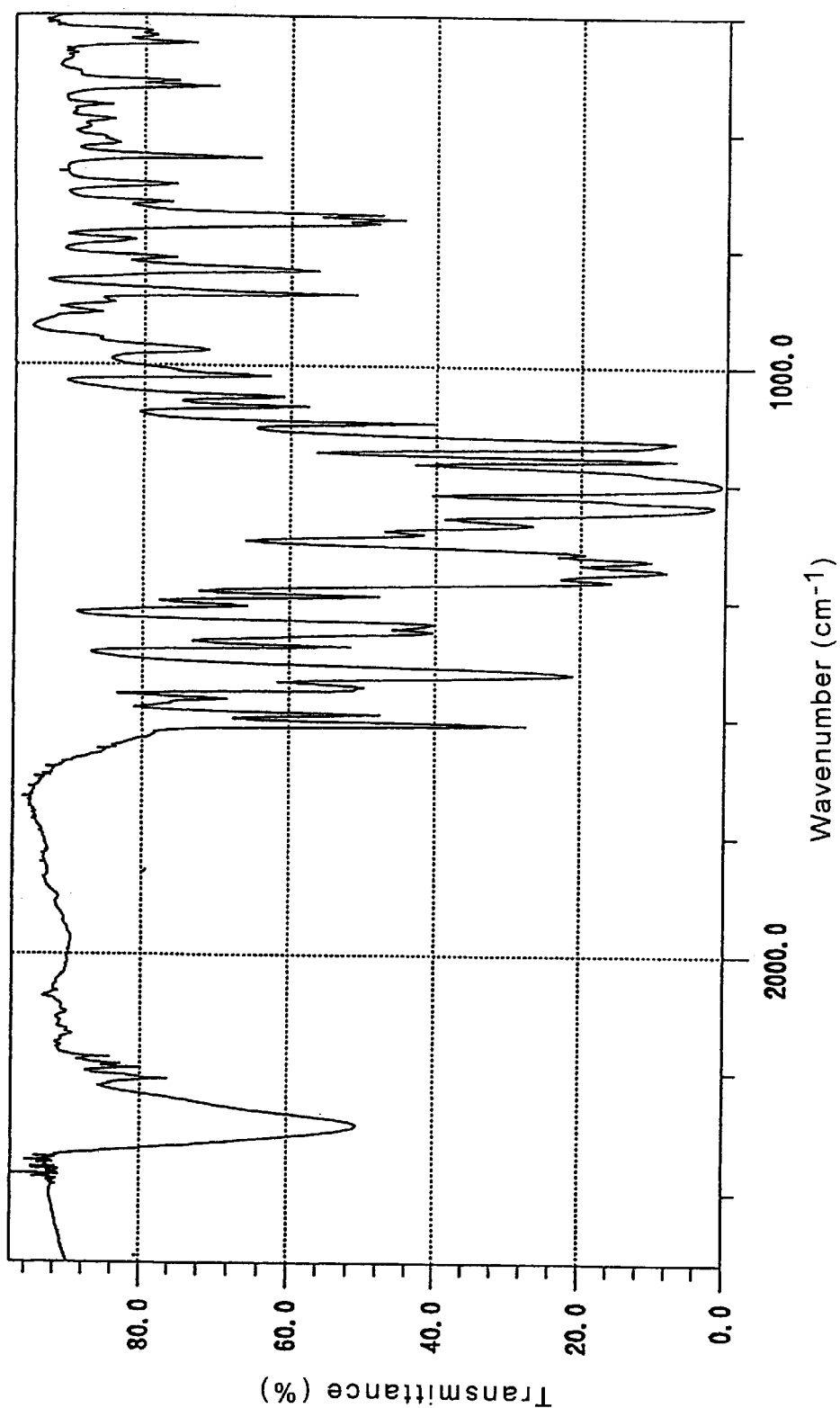
FIG. 7 is a graph illustrating an infrared spectrum of a metal-containing azo compound obtained in Example 26.

It is noted that in FIG. 1, the reference numerals denote the following elements:
1 . . . substrate, 2 . . . recording layer, 3 . . . reflective layer, 4 . . . adhesive layer, 5 . . . substrate, 6 . . . groove.

EMBODIMENTS OF THE INVENTION

The metal-containing azo compound according to the present invention is one in which two different azo compound ligands are bonded to the bivalent metal. That is, in the above formula (a1), (a2), (a3) or (a4), one residue is different from the other in at least one of the combination of $X^1$ and $X^2$ and the combination of $Y^1$ and $Y^2$. Here, in the formula (a1), (a2), (a3) or (a4), as generally used in the chemistry field, the solid line denotes a covalent bond and the arrow with a dashed line denotes a coordinate bond which is weaker than the covalent bond. Further, the formulae (a1), (a2), (a3) and (a4) show tautomerism of the metal-containing azo compound of the present invention. For the simplicity in the following, the description is made only in connection with the metal-containing azo compound corresponding to (a1), but such description is also applicable to the compounds corresponding to (a2) to (a4). Hereafter, the metal M, the residues $X^1$ and $X^2$ and the residues $Y^1$ and $Y^2$ which constitute the metal-containing azo compound of the present invention will be described.

In the aforementioned metal-containing azo compound, the metal M is not specifically limited as long as it is a bivalent metal, and it may be, for example, zinc, nickel, copper, manganese, iron, cobalt, palladium, platinum, tin or magnesium, and in particular zinc, nickel, copper or the like is preferable.

Each of the residues $X^1$ and $X^2$ forms the monocyclic or polycyclic aromatic ring together with the carbon atoms adjacent thereto at its both ends. Specifically, the residues $X^1$ and $X^2$ each preferably form a benzene ring, a phenanthrene ring or a naphthalene ring. Each of the residues $Y^1$ and $Y^2$ forms a nitrogen-containing aromatic heterocycle together with a nitrogen atom and carbon atoms that are adjacent thereto at its both ends, and preferably forms a pyridine ring, a pyrimidine ring, a pyrazine ring, a triazine ring, a thiazole ring, or a benzothiazole ring.

Further, when one or more residues selected from the residues $X^1$, $X^2$, $Y^1$ and $Y^2$ have a substituent(s) (instead of a hydrogen atom(s)), such substituent(s) is preferably selected from the group consisting of a halogen atom, a substituted and non-substituted alkyl group, a substituted and non-substituted alkoxyl group, a substituted and non-substituted alkylthio group, a substituted and non-substituted aryl group, a substituted and non-substituted aryloxyl group, a substituted and non-substituted arylthio group, a nitro group, and a substituted and non-substituted amino group.

Furthermore, the substituent(s) has carbon atom(s), its carbon number is preferably 1 to 15, more preferably 1 to 9, still more preferably 1 to 5, and most preferably 1 to 3. The substituent may be, for example, one of the following:

(1) the halogen atom which may be fluorine, chlorine, bromine, or iodine;

(2) the substituted or non-substituted alkyl group which may be a straight-chain or branched group such as a methyl group, an ethyl group, a propyl group, a butyl group, a pentyl group, a hexyl group, a heptyl group, an octyl group, a trifluoromethyl group, a trifluoroethyl group, a pentafluoropropyl group, or the like;

(3) the substituted or non-substituted alkoxyl group which may be a straight-chain or branched group such as a methoxyl group, an ethoxyl group, a propoxyl group, a butoxyl group, a pentyloxyl group, a trifluoromethoxyl group, a trifluoroethoxyl group, a pentafluoropropoxyl group, a bis(trifluoromethyl)propoxyl group, or the like;

(4) the substituted or non-substituted alkylthio group which may be a straight-chain or branched group such as a methylthio group, an ethylthio group, a tert-butylthio group, or the like;

(5) the substituted or non-substituted aryl group which may be a phenyl group, a naphthyl group, a pyrrole group, or the like;

(6) the aryloxyl group which may be a phenoxyl group or the like; and (7) the substituted or non-substituted amino group which may be an amino group, a diethylamino group, or the like.

The metal-containing azo compound according to the present invention is one wherein one residue is different from the other in at least one of the combination of $X^1$ and $X^2$ and the combination of $Y^1$ and $Y^2$, that is, two different azo compound ligands are bonded to the bivalent metal. Therefore, a compound wherein $X^1$ and $X^2$ are different from each other and the other parts in each ligand have the same structures is included in the metal-containing azo compound of the present invention.

The case where $X^1$ and $X^2$ are "different from each other" includes a case where their structures are thoroughly different from each other (for example, one is a benzene ring and the other is a naphthalene ring) as well as a case where while both of them have the same basic skeleton (such as a naphthalene ring), the substituents are different from each other, or the substituents are the same, however the sites of the substituents are different. In other words, the case where $X^1$ and $X^2$ are "different from each other" includes the following cases: the case where groups (including residues and substituents bonded to the residues) are different from each other in the combination of $X^1$ and $X^2$; the case where a group bonded to one residue and an atom bonded to the other residue are different in such combination; and the case where atoms bonded to each residue are different from each other in such combination. These are applicable to the relationship between $Y^1$ and $Y^2$.

According to the present invention, in the general formulae (a1) to (a4), substituents $R^1$ and $R^2$ are preferably bonded to the carbon atoms respectively which are adjacent to the residues $Y^1$ and $Y^2$ respectively and not bonded to the azo groups respectively (i.e. each substituent is preferably bonded to one of two carbon atoms adjacent to $Y^1$ or $Y^2$ which one is bonded to the nitrogen atom adjacent to the other carbon atom that is bonded to the azo group). That is, the compound is preferred which is represented by the following general formulae (a1') to (a4'):

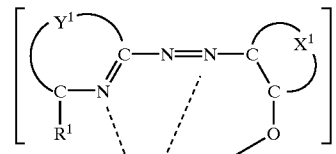

formula (a1')

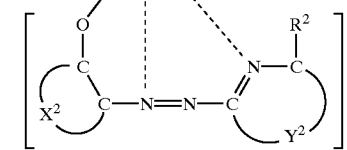

formula (a2')

-continued

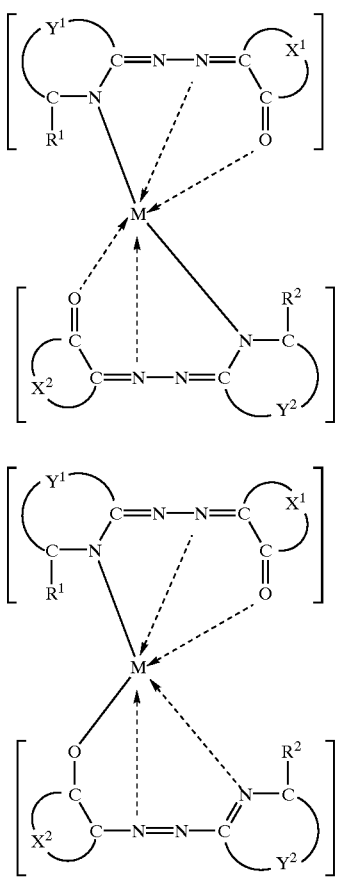

formula (a3')

formula (a4')

The substituents $R^1$ and $R^2$ are each selected from the group consisting of a hydrogen atom, a substituted and non-substituted alkyl group, a substituted and non-substituted alkoxyl group, a substituted and non-substituted alkylthio group, a substituted and non-substituted aryl group, a substituted and non-substituted aryloxyl group, and a substituted and non-substituted arylthio group. $R^1$ and/or $R^2$ is preferably selected from the group consisting of a substituted and non-substituted alkyl group having 1 to 9 carbon atoms, a substituted and non-substituted alkoxyl group having 1 to 9 carbon atoms, a substituted and non-substituted alkylthio group having 1 to 9 carbon atoms, a substituted and non-substituted aryl group having 6 to 9 carbon atoms, a substituted and non-substituted aryloxyl group having 6 to 9 carbon atoms, and a substituted and non-substituted arylthio group having 6 to 9 carbon atoms. In the present invention, more preferable groups $R^1$ and $R^2$ are each an alkyl group having 1 to 9 carbon atoms; still more preferable groups $R^1$ and $R^2$ are each an alkyl group having 1 to 5 carbon atoms; and most preferable groups $R^1$ and $R^2$ are each an alkyl group having 1 to 3 carbon atoms. The groups $R^1$ and $R^2$ may be straight-chain or branched. Preferable groups $R^1$ and $R^2$ are each specifically a methyl group, an ethyl group, a butyl group, a pentyl group, a hexyl group, a heptyl group, an octyl group, a methoxyl group, an ethoxyl group, a propoxyl group, a butoxyl group, a pentyloxyl group, an aryloxyl group (such as phenoxyl group), a methylthio group, an ethylthio group, a butylthio group, an arylthio group (such as phenylthio group), or a phenyl group. Each of the groups $R^1$ and $R^2$ may or may not have a substituent(s).

Further, when the group $R^1$ and/or $R^2$ has a substituent(s), a preferable embodiment of the group is a fluoromethyl (such as trifluoromethyl), a fluoroethyl (such as trifluoroethyl), a fluoropropyl (such as pentafluoropropyl), a fluoromethoxyl (such as trifluoromethoxyl), a fluoroethoxyl (such as trifluoroethoxyl), a fluoropropoxyl (such as bis(trifluoromethyl)propoxyl or 2,2,3,3,3-pentafluoropropoxyl), or a fluoromethylphenoxyl (such as 4-trifluoromethylphenoxyl) group.

In the present invention, one of $R^1$ and $R^2$ may be a hydrogen atom, or both of $R^1$ and $R^2$ may be hydrogen atoms.

It should be noted that each of the residues $Y^1$ and $Y^2$ in the compound represented by the general formulae (a1') to (a4') preferably forms a pyridine ring, a pyrimidine ring, a pyrazine ring, a triazine ring, or a thiazole ring together with the nitrogen atom and the carbon atoms that are adjacent thereto at its both end. Further, for example, the compound may be one wherein only the residue $Y^1$ forms a benzothiazole group together with the adjacent carbon atoms and does not have the group $R^1$, while only the residue $Y^2$ has the group $R^2$.

Also when the metal-containing azo compound represented by the general formulae (a1) to (a4) have the groups $R^1$ and $R^2$ at the predetermined sites, it is necessary that the compound has two different azo compound ligands which are boned to a bivalent metal. That is, when the compounds has $R^1$ and $R^2$, it is necessary that in at least one of the combination of residues $X^1$ and $X^2$, the combination of residues $Y^1$ and $Y^2$, and the combination of substituents $R^1$ and $R^2$, the residues or the substituents are different from each other. The meaning of "different from each other" is as described above in connection with the combination of $X^1$ and $X^2$ as an example.

In order to describe the metal-containing azo compound of the present invention more specifically, some examples of the azo compound ligands to be bonded to the metal are shown. In the following, X is used to generically refer to $X^1$ and $X^2$, Y is used to generically refer to $Y^1$ and $Y^2$, and R is used to generically refer to $R^1$ and $R^2$. Further, for the simplicity of understanding, all ligands are shown bonded to the metal M.

The first preferred azo compound ligand is 1-(6-substituted-2-pyridylazo)-2-naphtholato represented by the formula (b):

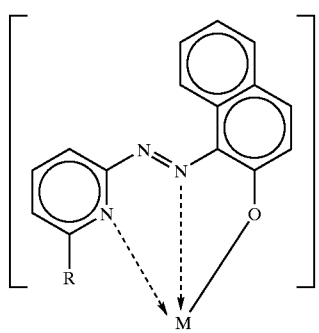

(b)

wherein the residue X forms a naphthalene ring together with the adjacent carbon atoms, the residue Y forms a pyridine ring together with the nitrogen atom and the carbon atoms that are adjacent thereto, and the substituent R is bonded to the carbon atom that is adjacent to the residue Y.

The second preferred azo compound ligand is 10-(6-substituted-2-pyridylazo)-9-phenanthrolato represented by the formula (c):

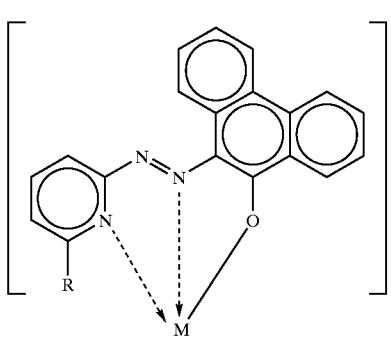
(c)

wherein the residue X forms a phenanthrene ring together with the adjacent carbon atoms, the residue Y forms a pyridine ring (pyridyl group) together with the nitrogen atom and the carbon atoms that are adjacent thereto, and the substituent R is bonded to the carbon atom that is adjacent to the residue Y.

Further, in the formula (b) or (c), instead of the pyridyl group, a pyrimidinyl group (or a pyrimidine ring) represented by the formula (d):

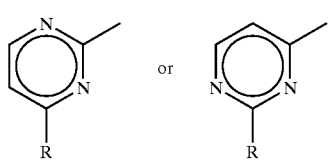
(d)

may be included.

Furthermore, in the formula (b) or (c), instead of the pyridyl group, a pyrazinyl group (or a pyrazine ring) represented by the formula (e):

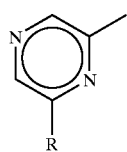
(e)

may be included.

In addition, in the formula (b) or (c), instead of the pyridyl group, a triazinyl group (or a triazine ring) represented by the formula (f):

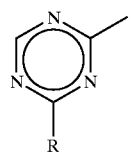
(f)

may be included.

Additionally, in the formula (b) or (c), instead of the pyridyl group, a thiazolyl group (or a thiazole ring) represented by the following formula (g):

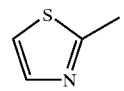
(g)

may be included.

Also, in the formula (b) or (c), instead of the pyridyl group, a benzothiazolyl group (or a benzothiazol ring) represented by the following formula (h):

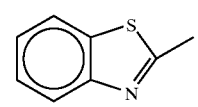
(h)

may be included. In this case, a substituent cannot be bonded to the carbon atom adjacent to the nitrogen atom because of the structure of benzothiazolyl group.

It should be noted that a sulfur atom may be included instead of the oxygen atom bonded to the carbon atom that is adjacent to the residue X. That is, the phenanthrene or naphthalene ring may be a thiophenanthrene or thionaphthalene ring.

More specifically, the azo compound ligands represented by the following formulae (i) to (n) can be bonded to the metal:

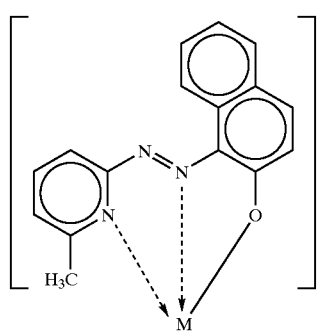
(i)

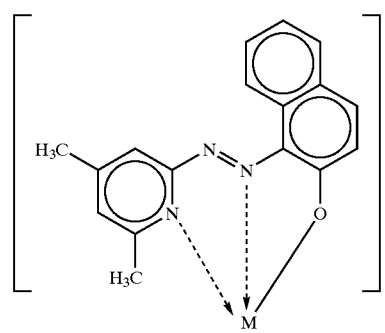
(j)

-continued

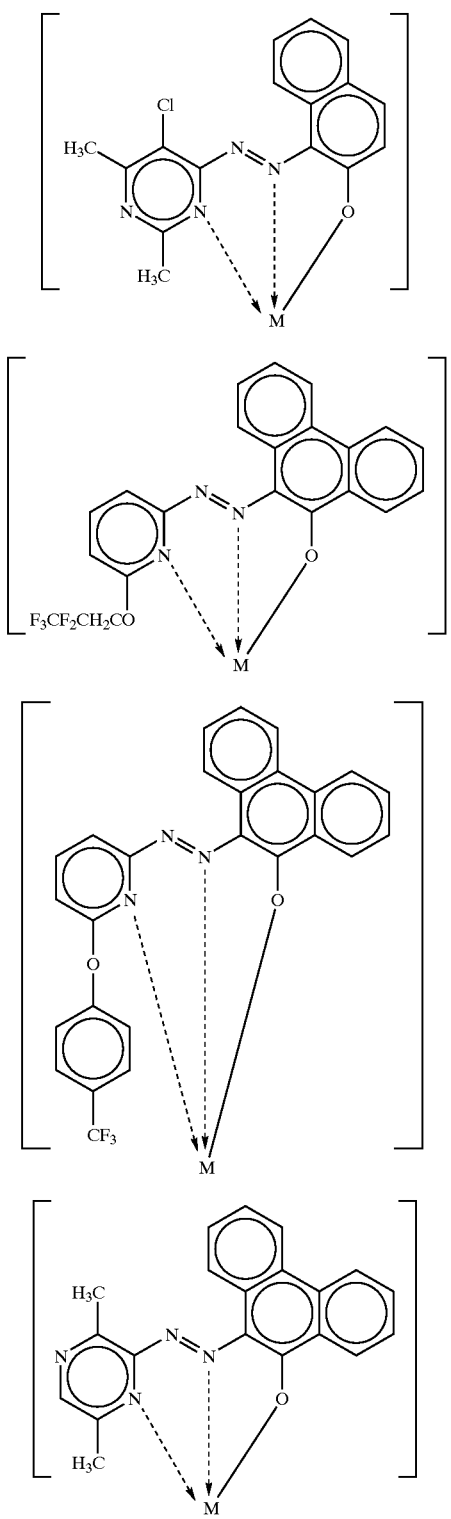

In the metal-containing azo compound of the present invention, two different azo compound ligands which are selected from the azo compound ligands represented by, for example, the above formulae (i) to (n), are bonded to the bivalent metal. An azo compound as a ligand can be synthesized by a conventional method, such as coupling reaction or oxidation of a substituted hydrazine. The metal-containing azo compound of the present invention can be synthesized by selecting 1-(6-substituted-2-pyridylazo)-2-naphthol and 1-(2-pyridylazo)-2-naphthol as the azo compounds which constitute the ligands and reacting such azo compounds with a metal salt in an appropriate solvent while heating. For example, an acetate, a chloride or a carbonate can be used as the metal salt. For example, methanol or a mixed solvent of methanol and dioxane can be used as the solvent. A preferable metal salt is the acetate. It suffices to mix equimolecular quantities of each of the two different azo compounds and the metal salt, however in some cases it is necessary to double the mole ratio of one of the azo compounds.

Next, an optical recording medium of the present invention in which the metal-containing azo compound of the present invention is used is described.

The optical recording medium of the present invention may comprise at least a recording layer, a reflective layer and a protective layer that are successively formed on a substrate. The optical recording medium of the present invention includes the metal-containing azo compound which is represented by at least one formula selected from the above general formulae (a1), (a2), (a3) and (a4) as a dyestuff which forms the recording layer. As long as this condition is satisfied, the recording layer comprises two or more metal-containing azo compounds each of which is represented by at least one formula selected from the above general formulae (a1), (a2), (a3) and (a4).

Further, the optical recording medium may contain a component(s) other than the metal-containing azo compound of the present invention in the recording layer. The recording layer may contain, for example, a metal-containing azo compound wherein $X^1$ and $X^2$ are the same, $Y^1$ and $Y^2$ are the same, and $R^1$ and $R^2$ are the same, i.e. the same two azo compound ligands are bonded to the metal, or may contain at least one of other known components used as a dyestuff and/or components that improve the properties of the recording layer (for example, a light resistance improver or a stabilizer).

In the optical recording medium of the present invention, the metal-containing azo compound which forms the recording layer may be applied according to any conventional method (i.e. a wet process or a dry process) which is carried out in production of CD or DVD. When the wet process is employed, a fluoroalcohol (such as 1,1,3-trihydrotetrafluoropropanol available from Daikin Industries Ltd. under the tradename "Fluoroalcohol N1"), cellosolve solvent (such as ethylcellosolve) or the like can be used as a solvent into which the metal-containing azo compound is dissolved. The wet process itself is well known and, for example, the conventional method (such as a spin coat method) can be used for the wet process, and no more detailed explanation is necessary.

When the dry process is employed, vacuum vapor deposition in particular is preferably used. This is a process wherein a dyestuff is heated to melt and evaporate or directly sublimated under a high vacuum of not more than $10^{-3}$ Torr; and the evaporated dyestuff is condensed on a substrate and thereby a thin film (i.e. the recording layer) is formed on the substrate. When the recording layer is formed by the vacuum vapor deposition, the organic dyestuff evaporated or sublimed from an evaporation source is deposited to form a uniform film over the entire surface of the substrate which film follows the groove shape of the substrate.

As a result, the difference in level of the layers between on the groove portion of the substrate and on the inter-groove portion is determined by an initial depth of the groove in the substrate, so that the tracking error signals can be adjusted by the groove depth of the substrate. Hereafter, the optical recording medium having the recording layer formed on the substrate by the vacuum vapor deposition of the dyestuff is referred to as a "vapor deposition type" one. Thus, in the vapor deposition type, the same level of tracking error signals as the application-type optical recording medium can be sufficiently obtained even if the groove of the substrate has a smaller depth. Accordingly, when the groove of the substrate is able to have a small depth, there will be little radial groove-depth inclination generated upon molding the substrate or little radial recording-layer thickness inclination caused by change in a solution viscosity upon applying the organic dyestuff solution. Thus, forming the recording layer through the vacuum vapor deposition provides an additional advantage in that stable properties with little change are obtained over the entire surface of the substrate.

Such vapor deposition method is known in the art, and no more detailed explanation is necessary. For the details, reference is made, for example, to Japanese Patent Application No. 54-164627 disclosing a method of vapor-depositing a phthalocyanine dye on a substrate, the disclosure of which is incorporated herein by the reference.

In a recording layer of the conventional CD-R, cyanine-based organic dyestuffs are used. These dyestuffs can be adapted to shorter laser wavelengths used for the DVD, by adjusting the length of a methine chain in a molecule center, the kind of an aromatic ring or heterocycle at a molecule end, the kind of a substituent bonded thereto, or the like. However, since many of these have counter ions and are liable to be decomposed when they are vaporized under vacuum, they cannot be used as they are. In other words, for the vacuum vapor deposition, dyestuffs that do not have counter ions are suitable, and particularly the metal-containing azo compounds that do not have counter ions, such as those used in the optical recording medium of the present invention, are suitable.

Intensive studies of the vapor deposition of metal-containing azo compounds have shown that the metal-containing azo compound of the present invention has a sublimation or evaporation starting temperature within the range of 100 to 300° C. under a low pressure (high vacuum) of not more than $10^{-3}$ Torr. It should be noted that in the present specification, the sublimation or evaporation starting temperature refers to the following temperature of an evaporation source (evaporation vessel) containing a compound to be evaporated. The temperature is measured by a temperature monitor comprising a thermocouple or the like when the evaporation source is gradually heated under a low pressure (high vacuum) of not more than $10^{-3}$ Torr and the evaporation rate of the compound becomes 1 Å/s, which is measured by a thickness monitor of quartz oscillator type.

In the production of the optical recording medium according to the present invention, a compound suitable for the vapor deposition preferably has, for example, a decomposition temperature of about 300 to 500° C. When the decomposition temperature of the metal-containing azo compound is less than 300° C., the difference between the sublimation or evaporation starting temperature and the decomposition temperature is small, so that the dyestuff is easily decomposed, which leads to poor film formation. On the other hand, when the decomposition temperature is higher than 500° C., a high recordation power is needed for decomposing the dyestuff, which deteriorates the properties of the optical recording medium. Therefore, the decomposition temperature of the metal-containing azo compound used in the vapor deposition type is appropriately in the range of 300 to 500° C. in general. The decomposition temperature of the metal-containing azo compound used in the present invention is within such range. It should be noted that the decomposition temperature is a temperature measured by a differential scanning calorimetry (DSC) and refers to a temperature at which a sample begins to be chemically decomposed, i.e. a temperature at which a heat generation peak appears, when the sample is heated in an inert gas of 1 atm by raising a temperature at a constant rate.

Further, in view of the productivity, the metal-containing azo compound preferably has a sublimation or evaporation rate of not less than 200 Å/min as a thickness growing speed of the optical recording layer. In the present specification, the sublimation or evaporation rate refers to the maximum amount (or thickness) of a film formed per one minute, as determined by measuring with a film thickness monitor of a quartz oscillator type the change in the thickness of the film formed when 0.1 g of a dyestuff is evaporated by heating an evaporation source in a high vacuum of not more than $10^{-3}$ Torr at a temperature elevation rate of 40° C./min.

Generally, taking the productivity into consideration, the rate of vapor-depositing the recording layer-constituting dyestuff, i.e. the film forming rate, is preferably set at not less than about 1000 Å/min. For this purpose, the metal-containing azo compound must be heated so that the temperature thereof becomes high. Therefore, if the sublimation or evaporation rate of the compound is small, a considerable amount of heat is required in increasing the film-forming rate. This results in a disadvantage that the heating temperature of the metal-containing azo compound approaches to its decomposition temperature, causing the denaturing of the metal-containing azo compound to be easily started. If the metal-containing azo compound is denatured, recordation/reproduction of the signals of short pits will be particularly difficult, leading to deteriorated properties of the optical recording medium such as low resolution that is a ratio of a reproduction output from the shortest pit/a reproduction output from the longest pit. Accordingly, it is preferable that the metal-containing azo compound used in the present invention is somewhat easily sublimed or evaporated.

Upon the vapor deposition, the heating temperature (i.e. sublimation or evaporation temperature) of the metal-containing azo compound used in the present invention is preferably set at a temperature lower than the decomposition temperature by 50 to 100° C. In particular, when the sublimation or evaporation rate of the metal-containing azo compound is not less than 200 Å/min, a sufficient film-forming rate (film-forming speed) can be achieved even if the heating temperature is set as described above, whereby the optical recording medium can be produced with good productivity.

Generally, a suitable film-forming rate is from 200 to 4000 Å/min. This rate is achieved by suitably adjusting the operation conditions such as the operation pressure, the heating temperature, and the amount of heat to be added. In adjusting the operation conditions, care should be taken not to denature or decompose the dyestuff.

Generally, in the optical recording medium of the present invention, the thickness of the recording layer is preferably within the range of 40 to 300 nm. When the recording layer has a thickness smaller than 40 nm, the output from the optical recording medium is generally small, whereas when the thickness is larger than 300 nm, the reflectivity generally decreases, thereby deteriorating the properties of the optical recording medium.

Further, in the optical recording medium of the present invention, the thickness of the reflective layer is preferably within the range of 30 to 200 nm. When the reflective layer has a thickness smaller than 30 nm, the reflectivity generally decreases, whereas when the thickness is larger than 200 nm, the reflectivity is saturated, which is disadvantageous in terms of costs and productivity.

In the optical recording medium of the present invention, the substrate has the spiral groove. Generally, the ratio of the groove width ($\mu$m) thereof and the track pitch (TP) ($\mu$m), and the groove depth (nm) in case where the wavelength of the laser beam used for recordation is represented by $\lambda$ (nm) and the refractive index of the substrate is represented by "n", are preferably within the following ranges:

0.25 ≦ groove width/TP ≦ 0.45

0.2$\lambda$/(4n) ≦ groove depth ≦ 0.8$\lambda$/(4n).

When the groove width/TP is smaller than 0.25, the tracking error signals generally decrease, whereas when the groove width/TP is larger than 0.45, the radial contrast generally decreases, whereby the properties of the optical recording medium are deteriorated. Further, when the groove depth is smaller than 0.2$\lambda$/(4n), the tracking error signals generally decrease, whereas when the groove depth is larger than 0.8$\lambda$/(4n), the reflectivity generally decreases, whereby the properties of the optical recording medium are deteriorated. Here, "TP", "groove width" and "groove depth" are used to mean the meanings which are conventionally used in the field of the art.

Hereafter, one embodiment of the optical recording medium of the present invention will be explained in detail with reference to FIG. 1.

FIG. 1 shows an enlarged schematic view illustrating a portion of a cross section of an optical recording medium of the present invention. A substrate (1) is made of a transparent resin such as polycarbonate, with a spiral groove (6) formed on one surface of the substrate. A recording layer (2) containing the metal-containing azo compound and a reflective layer (3) made of gold or the like are successively formed on the surface of the substrate (1) on which the groove is formed. A protective layer made of an ultraviolet-curable resin or the like may be formed thereon. Alternatively, a substrate (5) made of polycarbonate may be adhered with an adhesive layer (4) made of an ultraviolet-curable resin.

The substrate (1) is preferably transparent to a laser beam, i.e. a substrate that transmits the laser beam, and may be made of a glass or a plastic. For example, the substrate may be formed of an acrylic resin, an epoxy resin, a polyolefin resin, a polycarbonate resin, or a material having optical and mechanical properties equivalent thereto. The substrate may be a simple plate or a composite plate. If the substrate is a composite plate, it may be a laminate of stuck layers. Further, the substrate (5) may be made of the same material as the substrate (1) or of other material as long as it does not deteriorate the mechanical properties of the optical recording medium.

As described in the above, the spiral groove formed on the substrate (1) has a width such that the groove width/TP is preferably within the range of 0.25 to 0.45, and more preferably within the range of 0.30 to 0.45. Further, the groove depth in case where the wavelength of the laser beam is represented by "$\lambda$" and the refractive index of the substrate is represented by "n", is preferably within the range of 0.2$\lambda$/(4n) to 0.8$\lambda$/(4n), and more preferably within the range of 0.3$\lambda$/(4n) to 0.6$\lambda$/(4n).

The recording layer (2) is constituted of the above-mentioned metal-containing azo compound. It should be noted that the above-exemplified metal-containing azo compound to be used for constituting the recording layer of the optical recording medium of the present invention is not necessarily used alone. Two or more of these metal-containing azo compounds may be used in the form of a mixture layer or laminated layers as long as they do not deteriorate the properties of the optical recording medium. Furthermore, other dyestuff may be used in combination, and it is possible to use, for example, polymethine dyes (cyanine dyes, merocyanine dyes, styryl dyes, squarilium dyes, and aminovinyl dyes), triphenylmethane dyes, fluorane dyes, quinone dyes, cationic dyes, macrocyclic azaannulene dyes (phthalocyanine dyes, naphthalocyanine dyes, porphyrin dyes and subphthalocyanine dyes), indophenol dyes, condensed ring dyes such as perylene or the like, in the mixture layer or the laminated layers.

The recording layer made of the mixture of two or more kinds of dyes is formed by vapor-depositing the dyes mixed beforehand or by multi-element vapor deposition. Here, the multi-element vapor deposition refers to the vapor deposition performed by using a plurality of evaporation sources and evaporating or subliming the dyes simultaneously from the evaporation sources. The recording layer in the form of the laminate is formed by repetition of vapor deposition steps.

The reflective layer (3) can be formed by using a material having a high reflectivity and an excellent environmental resistance, such as humidity resistance. For example, the reflective layer (3) can be formed as a film of Au, Ag, Al, Cu, Cr, Pt, Ni, Ti, or an alloy thereof by sputtering, vacuum vapor deposition, or the like. Among these, it is preferable to use Au, Ag, or Al. In case where recordation is carried out with a laser beam of a shorter wavelength, it is preferable to use Ag or Al having a small change in the reflectivity. The reflective layer (3) preferably has a thickness of 30 to 200 nm, and more preferably 50 to 100 nm.

The adhesive layer (4) is formed of an ultraviolet-curable resin made of a polymer material such as an epoxy resin, a urethane resin, an acrylic resin, a silicone resin, and the like.

Basically, the materials other than the metal-containing azo compound to be used in the recording layer may be any known ones as long as they do not deteriorate the properties of an optical recording medium.

EXAMPLES

Hereafter, description will be made as to examples of producing metal-containing azo compounds of the present invention and performance evaluation of optical recording media in which the metal-containing azo compounds were used. Here, in the synthesis of the metal-containing azo compounds, the compound obtained in each example was identified with the use of infrared spectrophotometry, mass spectrometry, NMR, and elementary analysis so as to confirm that the intended compound was obtained.

Synthesis of Azo Compound to be Bonded to a Metal (1) Production of 1-(6-methyl-2-pyridylazo)-2-naphthol (No. L21)

A reaction flask equipped with a cooling tube and a stirrer was loaded with 2-amino-6-methylpyridine (50 g), ethanol (250 ml), and sodium ethoxide (9.4 g), followed by dropwise addition of isopentyl nitrite (54 g) to the flask in 30 minutes with stirring. The resultant mixture was heated and further stirred at 75 to 80° C. for 4 hours for reaction. Thereafter, the heating was stopped, and the reaction mixture was cooled to room temperature, followed by dropwise addition of 2-naphthol (33.0 g) dissolved in ethanol (50 ml) in 30 minutes to the mixture. The resultant mixture was stirred at room temperature for one hour, heated, and stirred at 75 to 80° C. for additional two hours, followed by stopping the heating and then leaving the mixture to stand overnight. The reaction mixture was filtrated to remove insoluble components, and the filtrate was condensed by an evaporator for solidification. The resultant was dissolved in ethyl acetate (500 ml) and, after being successively washed with an aqueous solution of sodium hydroxide and water, the ethyl acetate layer (phase) was condensed by an evaporator, followed by addition of methanol to the residue for crystallization. The resultant was filtrated and the crystals were dried to give intended red orange crystals (2.1 g).

(2) Production of 1-(3-chloro-5-(trifluoro-methyl)-2-pyridylazo)-2-naphthol (No. L26)

A reaction flask was loaded with 3-chloro-5-(trifluoromethyl)-2-aminopyridine (4.0 g), ethanol (13 ml), and sodium ethoxide (1.4 g), followed by dropwise addition of isopentyl nitrite (2.9 g) to the flask in 30 minutes with stirring. After the dropwise addition was ended, heating was started and the mixture was stirred at 75 to 80° C. for four hours. The heating was stopped, and the reaction mixture was cooled to room temperature, followed by dropwise addition of 2-naphthol (1.7 g) dissolved in ethanol (5 ml) to the mixture in one hour. The resultant mixture was stirred at room temperature for one hour, heated, and stirred at 75 to 80° C. for additional one hour, followed by stopping the heating and then leaving the mixture to stand overnight. The reaction mixture was filtrated to remove insoluble components, and the filtrate was condensed by an evaporator. The residue was dissolved in ethyl acetate (100 ml) and, after being successively washed with an aqueous solution of sodium hydroxide and water, the ethyl acetate layer was condensed by an evaporator, followed by addition of methanol to the residue for crystallization. The resultant was filtrated and the crystals were dried to give intended red orange crystals (1.9 g).

(3) Production of 1-(3-butoxy-2-pyridylazo)-2-naphthol (No. L29)

A reaction flask was loaded with 2-amino-3-hydroxypyridine (8 g), dimethylformamide (DMF) (50 ml), and anhydrous potassium carbonate (12 g), and the temperature was raised up to 50° C. with stirring, followed by dropwise addition of n-butylbromide (11.9 g) to the flask in 4 hours with stirring. Then, the mixture was stirred at 60° C. for 2 hours. The heating was stopped, and water (200 ml) was added to the mixture. Ethyl acetate was added to the mixture and the mixture was stirred, followed by collecting the ethyl acetate layer with a separating funnel. The layer was condensed by an evaporator to precipitate crystals, and then the crystals were broken up with hexane. The crystals were filtrated for collection and dried to give crystals of 2-amino-3-butoxypyridine (5 g).

Next, a reaction flask was loaded with the crystals of 2-amino-3-butoxypyridine (4.4 g), ethanol (25 ml), and sodium ethoxide (2.2 g), followed by dropwise addition of isopentyl nitrite (3.8 g) to the flask in 30 minutes with stirring. The resultant mixture was heated and stirred at 75 to 80° C. for four hours for reaction. The heating was stopped, and the reaction mixture was cooled to room temperature, followed by dropwise addition of 2-naphthol (2.6 g) dissolved in ethanol (10 ml) to the mixture in 10 minutes. The resultant mixture was stirred at room temperature for one hour, heated, and stirred at 75 to 80° C. for additional two hours, followed by stopping the heating and then leaving the mixture to stand overnight. The reaction mixture was condensed by an evaporator. The residue was dissolved in ethyl acetate and, after being successively washed with an aqueous solution of sodium hydroxide and water, the ethyl acetate layer was condensed by an evaporator, followed by addition of methanol to the residue for crystallization. The resultant was filtrated and the crystals were dried to give intended crystals (2.5 g).

(4) Production of 1-(3,5-dichloro-2-pyridylazo)-2-naphthol (No. L30)

A reaction flask was loaded with 3,5-dichloro-2-aminopyridine (40 g), ethanol (300 ml), and sodium ethoxide (14 g), followed by dropwise addition of isopentyl nitrite (28 g) to the flask in 30 minutes with stirring. After the dropwise addition was ended, heating was started and the mixture was stirred at 75 to 80° C. for four hours. The heating was stopped, and the reaction mixture was cooled to room temperature, followed by dropwise addition of 2-naphthol (17 g) dissolved in ethanol (50 ml) to the mixture in one hour. The resultant mixture was stirred at room temperature for one hour, heated, and stirred at 75 to 80° C. for three hours, followed by stopping the heating and then leaving the mixture to stand overnight. The reaction mixture was filtrated to remove insoluble components, and the filtrate was condensed by an evaporator. The residue was dissolved in ethyl acetate and, after being successively washed with an aqueous solution of sodium hydroxide and water, the ethyl acetate layer was condensed by an evaporator, followed by addition of methanol to the residue for crystallization. The resultant was filtrated and the crystals were dried to give intended crystals (10 g).

(5) Production of 10-(3,6-dimethyl-2-pyrazinylazo)-9-phenanthrol (No. L46)

A reaction flask was loaded with 2-chloro-3,6-dimethylpyrazine (10 g) and ethanol (15 ml), and heated up to 50° C. with stirring. To this, a mixture of hydrazine monohydrate (11.2 g) and ethanol (10 ml) was dropwise added in one hour. The temperature was raised to the reflux temperature, followed by stirring for six hours. The heating was stopped and the reaction mixture was condensed by an evaporator. The precipitated crystals were filtrated for collection and dried to give 2-hydrazino-3,6-dimethylpyrazine (2.7 g).

Next, a reaction flask was loaded with acetic acid (80 ml) and 9,10-phenanthrenequinone (4.0 g), and heated up to 90° C. with stirring to dissolve 9,10-phenanthrenequinone. To the resultant, the crystals of 2-hydrazino-3,6-dimethylpyrazine (2.7 g) was added in 20 minutes. After stirring at 90 to 100° C. for two hours, the reaction mixture was cooled and filtrated. An aqueous solution of sodium hydroxide was added to the filtrate with stirring so that crystals precipitated. The crystals were filtrated and washed with methanol, followed by being recrystallized with dioxane-water. The crystals were then filtrated and dried to give intended crystals (3.3 g).

(6) Production of 10-[3-chloro-5-(trifluoro-methyl)-2-pyridylazo]-9-phenanthrol (No. L56)

A reaction flask was loaded with 2,3-dichloro-5-(trifluoromethyl)pyridine (10.8 g) and ethanol (25 ml), followed by dropwise addition of hydrazine monohydrate (3 g) to the flask in 5 minutes with stirring. The resultant mixture was heated and stirred at 40 to 60° C. for 2.5 hours.

Thereafter, the heating was stopped, and the reaction mixture was left to cool. The precipitated white crystals were filtered for collection and dried to give 3-chloro-2-hydrazino-5-(trifluoromethyl)-pyridine (7.5 g).

Next, a reaction flask was loaded with acetic acid (15 ml) and 9,10-phenanthrenequinone (5.0 g), and the temperature was raised to 100° C. with stirring to dissolve 9,10-phenanthrenequinone. To the resultant, the crystals of 3-chloro-2-hydrazino-5-(trifluoromethyl)-pyridine (5.0 g) was added in 30 minutes. After stirring at 100 to 105° C. for one hour, the reaction mixture was filtered. After being washed with methanol, the obtained crystals were dried to give intended crystals (5.6 g).

(7) Production of 10-(3,5-dichloro-2-pyridylazo)-9-phenanthrol (No. L70)

A reaction flask was loaded with 2,3,5-trichloropyridine (9.1 g) and ethanol (25 ml), followed by dropwise addition of hydrazine monohydrate (3 g) to the flask in 5 minutes with stirring. The resultant mixture was heated and stirred at 50 to 60° C. for 5 hours. Thereafter, the heating was stopped, and the reaction mixture was left to cool. The precipitated white crystals were filtered for collection and dried to give 3,5-dichloro-2-hydrazinopyridine (6.3 g).

Next, a reaction flask was loaded with acetic acid (15 ml) and 9,10-phenanthrenequinone (5.0 g), and the temperature was raised to 105° C. with stirring to dissolve 9,10-phenanthrenequinone. To the resultant, the crystals of 3,5-dichloro-2-hydrazinopyridine (4.6 g) was added in 30 minutes. After stirring at 105 to 110° C. for one hour, the reaction mixture was filtered. The filtrated crystals were washed with methanol, and then dried to give intended crystals (5.1 g).

(8) Production of 10-[6-(4-trifluoromethyl-phenoxy)-2-pyridylazo]-9-phenanthrol (No. L57)

A reaction flask was loaded with 4-trifluoromethylphenol (8.4 g), anhydrous potassium carbonate (8.6 g), and DMF (15 ml), followed by stirring at room temperature for 15 minutes. To this mixture, 2,6-difluoropyridine (6.0 g) dissolved in DMF (15 ml) was dropwise added in one hour. Thereafter, the temperature was raised up to 60° C., and the mixture was stirred for six hours. Water was added to the reaction mixture, and extraction was carried out with hexane, followed by addition of magnesium sulfate to the extracted liquid for drying. After filtration to remove magnesium sulfate, hexane was removed by an evaporator to give 2-fluoro-6-(4-trifluoromethylphenoxy)-pyridine (8.0 g).

Next, a reaction flask was loaded with 2-fluoro-6-(4-trifluoromethylphenoxy)pyridine (8.0 g) and ethanol (60 ml), and heated up to 40° C. with stirring. To this mixture, hydrazine monohydrate (7.6 g) was dropwise added in 30 minutes. The temperature of the mixture was raised to the reflux temperature, followed by stirring for 20 hours. Thereafter, the heating was stopped, and the reaction mixture was cooled, followed by filtration to remove insoluble components. The filtrate was condensed by an evaporator to give 2-hydrazino-6-(4-trifluoromethylphenoxy)pyridine (4.0 g).

Then, a reaction flask was loaded with acetic acid (30 ml) and 9,10-phenanthrenequinone (2.0 g), and the temperature was raised to 100° C. with stirring to dissolve 9,10-phenanthrenequinone. To this mixture, 2-hydrazino-6-(4-trifluoromethylphenoxy)pyridine (3.0 g) was added in 15 minutes. After stirring at 95 to 105° C. for two hours, the reaction mixture was filtrated. The filtrated crystals were successively washed with hot water and hot methanol, followed by recrystallization with dioxane-water to give crystals, which were then filtrated and dried to give intended crystals (3.5 g).

(9) Production of 10-[6-(2,2,3,3,4,4,5,5-octafluoropentyloxy)-2-pyridylazo]-9-phenanthrol (No. L65)

A reaction flask was loaded with 2,2,3,3,4,4,5,5-octafluoropentanol (16.1 g), DMF (42 ml), anhydrous potassium carbonate (9.6 g), followed by stirring at room temperature for one hour. To this mixture, 2,6-difluoropyridine (8.0 g) was dropwise added. The temperature was raised to 60° C., and the mixture was stirred for four hours. The heating was stopped, and water was added to the reaction mixture, followed by extraction with ethyl acetate. The extract was condensed by an evaporator to give 2-fluoro-6-(2,2,3,3,4,4,5,5-octafluoropentyloxy)-pyridine (20 g).

Next, a reaction flask was loaded with 2-fluoro-6-(2,2,3,3,4,4,5,5-octafluoropentyloxy)pyridine (10 g) and ethanol (8 ml), followed by dropwise addition of a mixture of hydrazine monohydrate (7.7 g) and ethanol (8 ml) to the flask in 30 minutes with stirring. After the dropwise addition was ended, stirring was continued at 55 to 65° C. for one hour. The heating was stopped, and water was added to the reaction mixture, followed by extraction with ethyl acetate. The extract was condensed to give 2-hydrazino-6-(2,2,3,3,4,4,5,5-octafluoropentyloxy)pyridine (10 g).

Next, a reaction flask was loaded with acetic acid (54 ml) and 9,10-phenanthrenequinone (3.8 g), and the temperature was raised to 110° C. with stirring to dissolve 9,10-phenanthrenequinone. To this mixture, 2-hydrazino-6-(2,2,3,3,4,4,5,5-octafluoropentyloxy)pyridine (10 g) was added in 30 minutes. After stirring at 110° C. for one hour, the reaction mixture was filtrated. Crystals were stirred in methanol (100 ml) for 30 minutes, filtrated and dried to give intended crystals (5.2 g).

(10) Production of 2-[6-methoxy-2-methyl-5-(trifluoromethyl)-4-pyrimidinylazo]-1-naphthol (No. L69)

A reaction flask was loaded with 1,1,3,3,3-pentafluoro-2-trifluoromethylpropyl methyl ether (18.1 g), acetamidine hydrochloride (11.1 g), dichloroethane (78 ml), water (78 ml), and benzyltriethylammonium chloride (0.078 g), and cooled to 0° C. with stirring. To this mixture, a 17% aqueous solution of sodium hydroxide (93 g) was dropwise added in 1.5 hours, followed by stirring for 1 hour. Thereafter, the cooling was stopped, and an organic layer was separated from the reaction mixture at room temperature and condensed to give 4-fluoro-6-methoxy-2-methyl-5-(trifluoromethyl)-pyrimidine (22 g). By GC/MS analysis, a molecular ion peak of 210 was confirmed for this compound.

Next, a reaction flask was loaded with 4-fluoro-6-methoxy-2-methyl-5-(trifluoromethyl)-pyrimidine (22 g) and ethanol (40 ml), followed by dropwise addition of hydrazine monohydrate (10.5 g) to the flask in one hour with stirring. Then, after stirring for one hour, the reaction mixture was filtrated to give 4-hydrazino-6-methoxy-2-methyl-5-(trifluoromethyl)pyrimidine. By GC/MS analysis, a molecular ion peak of 222 was confirmed for this compound.

Then, a flask was loaded with acetic acid (50 ml) and 1,2-naphthoquinone (2.9 g), and the temperature was raised up to 110° C. with stirring to dissolve 1,2-naphthoquinone.

To this mixture, 4-hydrazino-6-methoxy-2-methyl-5-(trifluoromethyl)pyrimidine (4 g) was added in 30 minutes. After stirring at 110° C. for 3 hours, the heating was stopped and left to cool. The reaction mixture was filtered. The filtrated crystals were recrystallized with dioxane to give crystals, which were then filtrated and dried to give intended crystals (2.3 g).

(11) Production of 10-[3,5-dichloro-4,6-bis(2,2,2-trifluoroethoxy)-2-pyridylazo]-9-phenanthrol (No. L77)

A reaction flask was loaded with 3,5-dichloro-2,4,6-trifluoropyridine (5.6 g), DMF (15 ml), and potassium carbonate (9.2 g), and heated up to 30° C. with stirring. To this, a mixture of 2,2,2-trifluoroethanol (5.6 g) and DMF (10 ml) was dropwise added in one hour. After the dropwise addition was ended, the temperature was raised to 50° C., followed by stirring for three hours. The heating was stopped and left to cool. Thereafter, water (100 ml) was added to the reaction mixture, followed by extraction with ether. The ether layer was condensed to give 3,5-dichloro-2-fluoro-4,6-bis(2,2,2-trifluoroethoxy)pyridine (9.7 g). By GC/MS analysis, a molecular ion peak of 362 was confirmed.

Next, a reaction flask was loaded with 3,5-dichloro-2-fluoro-4,6-bis(2,2,2-trifluoroethoxy)pyridine (9 g) and ethanol (30 ml), followed by dropwise addition of hydrazine monohydrate (2.5 g) to the flask in one hour with stirring. After the dropwise addition was ended, the temperature was raised up to 75° C., and the mixture was stirred for 3.5 hours. Thereafter, the heating was stopped, and the reaction mixture was condensed to give a solid. The solid was broken up with hexane and filtrated. The filtrated crystals were recrystallized with methanol-water to 3,5-dichloro-2-hydrazino-4,6-bis(2,2,2-trifluoroethoxy)pyridine (3.0 g). By GC/MS analysis, a molecular ion peak of 374 was confirmed.

Next, a reaction flask was loaded with acetic acid (30 ml) and 9,10-phenanthrenequinone (1.25 g), and the temperature was raised to 105° C. with stirring to dissolve 9,10-phenanthrenequinone. To this mixture, 3,5-dichloro-2-hydrazino-4,6-bis(2,2,2-trifluoroethoxy)pyridine (2.5 g) was added in 15 minutes. After stirring at 100 to 105° C. for two hours, the heating was stopped and the reaction mixture was left to cool and filtrated. The filtrated crystals were stirred for 30 minutes in methanol (100 ml), and then filtrated and dried to give intended crystals (2.3 g).

(12) Production of 10-(2-benzothiazolylazo)-9-phenanthrol (No. L45)

A reaction flask was loaded with acetic acid (50 ml) and 9,10-phenanthrenequinone (4.2 g), and the temperature was raised to 105° C. with stirring to dissolve 9,10-phenanthrenequinone. To this mixture, 2-hydrazinobenzothiazole (3.3 g) was added in three hours. After stirring at 100 to 110° C. for one hour, the reaction mixture was filtrated. The filtrated crystals were washed with methanol and dried to give intended crystals (3.9 g).

(13) Production of 1-(2-thiazolylazo)-2-naphthol (No. L08)

A reaction flask was loaded with 2-aminothiazole (3.1 g) and a 62% aqueous solution of sulfuric acid (17 g), followed by stirring to dissolve 2-aminothiazole. After dissolving, the reaction flask was cooled to 0° C. To this, a 45% sulfuric acid solution of nitrosyl sulfuric acid (8.8 g) was dropwise added at or below 5° C. in one hour. After the dropwise addition was ended, the mixture was stirred for additional two hours to give a diazonium compound. Another reaction flask was loaded with 2-naphthol (4.5 g), a 48% aqueous solution of sodium hydroxide (52 g) and water (130 ml), and cooled to 0° C. with stirring. To this, a solution of the above diazonium compound was dropwise added at or below 10° C. in 2 hours. After the dropwise addition was ended, the cooling was stopped, and the reaction mixture was stirred for 2 hours so that the temperature thereof returned to room temperature. The reaction mixture was neutralized with dilute sulfuric acid and stirred at about pH 8, followed by filtration. The filtrated crystals were recrystallized with methanol and dried to give intended crystals (4.2 g).

(14) Production of 10-(4-phenyl-2-thiazolylazo)-9-phenanthrol (No. L78)

A reaction flask was loaded with water (3.4 ml), a 98% aqueous solution of sulfuric acid (7.2 ml), 2-amino-4-phenylthiazol (1.66 g) and formic acid (1.6 ml) successively, followed by stirring to dissolve 2-amino-4-phenylthiazol. The liquid was cooled to 0° C., followed by dropwise addition of a solution in which sodium nitrite (0.47 g) was dissolved in water (2 ml) to the mixture in 10 minutes. After stirring at or below 5° C. for one hour, a solution in which 9-phenanthrol (3.2 g) was dissolved in ethanol (30 ml) was dropwise added to the mixture in one hour. The cooling was stopped and the reaction mixture at room temperature was filtrated to give crystals. The crystals were recrystallized with dioxane-methanol to give intended crystals (1.7 g).

(15) Production of 2-(3-chloro-5-trifluoromethyl-2-pyridylazo)-5-(diethylamino)phenol (No. L116)

A reaction flask was loaded with 2,3-dichloro-5-trifluoromethylpyridine (15 g) and ethanol (90 ml), followed by dropwise addition of hydrazine monohydrate (10.4 g) to the flask in one hour with stirring. After stirring overnight, the reaction mixture was filtered, and the filtrate was condensed to precipitate crystals. The crystals were filtrated for collection and air-dried to give 3-chloro-2-hydrazino-5-trifluoromethylpyridine (9.1 g).

Next, a reaction flask was loaded with 3-(N,N-diethlyamino)phenol (1.3 g), dimethylformamide (9 ml), acetic acid (3 ml) and iodine (0.14 g), and they were mixed, followed by addition of 3-chloro-2-hydrazino-5-trifluoromethylpyridine (1.0 g) to the flask with stirring. Then, to this mixture, a 30 % hydrogen peroxide water (1.4 g) was dropwise added in one hour and the mixture was stirred overnight. Water was added to this reaction mixture, followed by extraction with ether. The organic layer was condensed to precipitate crystals. The crystals were filtrated for collection and dried to give intended crystals (0.5 g).

(16) Production of 2-(3,5-dichloro-2-pyridylazo)-5-(diethylamino)phenol) (No. L126)

A reaction flask was loaded with 2,3,5-trichloropyridine (11.2 g) and ethanol (12 ml), followed by dropwise addition of hydrazine monohydrate. (9.2 g) to the flask in one hour with stirring. After stirring overnight, the reaction mixture was filtrated and the filtrate was condensed to precipitate crystals. The crystals were filtrated for collection and air-dried to give 3,5-dichloro-2-hydrazinopyridine (9.0 g).

Next, a flask was loaded with 3-(N,N-diethylamino)phenol (1.7 g), dimethylformamide (14 ml), acetic acid (5 ml) and iodine (0.24 g), and they were mixed, followed by addition of 3,5-dichloro-2-hydrazinopyridine (1.6 g) to the flask with stirring. Then, to this, a 30% hydrogen peroxide water (2.4 g) was dropwise added in 90 minutes and the mixture was stirred overnight. The reaction mixture was filtered, and ether and water were added to the filtrate, followed by stirring. After stirring, the ether layer was collected and condensed to precipitate crystals. The crystals were filtered for collection and dried to give intended crystals (0.54 g).

(17) Production of 1-(3-methoxy-2-pyridylazo)-2-naphthol (No. L140)

A reaction flask was loaded with 3-hydroxy-2-nitropyridine (20 g), dimethylformamide (80 ml), and potassium carbonate (23.4 g), and they were mixed, followed by dropwise addition of methyl iodide (52.4 g) to the flask in 2.2 hours. After stirring overnight, water was added to this for crystallization. The crystals were filtered for collection and dried to give 3-methoxy-2-nitropyridine (16.5 g).

Then, a reaction flask was loaded with this 3-methoxy-2-nitropyridine (9.0 g), sodium sulfide enneahydrate (64 g), ethanol (93 ml) and water (46 ml) and they were mixed, followed by stirring at 70° C. for 2.5 hours. Then, the mixture was cooled to room temperature. To this, toluene and water were added, followed by stirring. The organic layer was collected and washed with a saline solution, and then dried with sodium sulfate. This was filtered and the filtrate was condensed to give 2-amino-3-methoxypyridine (5.1 g).

Next, a reaction flask was loaded with sodium ethylate (2.2 g) and ethanol (33 ml) and they were mixed. To the mixture, 2-amino-3-methoxypyridine (3.3 g) was added, and then isopentyl nitrite (3.7 g) was dropwise added in ten minutes with stirring. This was heated and stirred at the reflux temperature for 3.5 hours. The heating was stopped, and the mixture was cooled to room temperature. To this, 2-naphthol (2.7 g) dissolved in ethanol (5 ml) was dropwise added in 30 minutes. After stirring at room temperature for one hour, this mixture was heated to the reflux temperature, followed by stirring for additional 3 hours. The reaction mixture was filtered and the filtrated crystals were recrystallized with methanol-water and further recrystallized with dioxane to give intended crystals (0.68 g).

(18) Production of 1-(3-propoxy-2-pyridylazo)-2-naphthol (No. L132)

A reaction flask was loaded with 2-amino-3-hydroxypyridine (12 g), dimethylformamide (75 ml), and potassium carbonate (18 g), and they were mixed. The temperature was raised to 50° C. To this mixture, 1-bromopropane (16.1 g) was dropwise added in 30 minutes. After stirring at 50° C. overnight, water and ether were added to the mixture, followed by stirring. The organic layer was collected from this, and washed with water, and then condensed to give 2-amino-3-propoxypyridine (4.0 g).

Next, a flask was loaded with sodium ethylate (1.6 g), ethanol (14 ml), and 2-amino-3-propoxypyridine (3.8 g), and they were mixed. To the mixture, isopentyl nitrite (2.7 g) was dropwise added in 20 minutes with stirring. This was stirred at the reflux temperature for 4 hours, and then cooled to room temperature. Thereafter, to this, 2-naphthol (2.0 g) dissolved in ethanol (5 ml) was dropwise added in one hour. After stirring at room temperature for two hours, this mixture was heated to the reflux temperature, followed by stirring for additional 2 hours. The reaction mixture was filtered and the filtrate was condensed to precipitate crystals. The crystals were filtered for collection and recrystallized with dioxane-water to give intended crystals (0.59 g).

(19) Production of 1-(3-methyl-2-pyridylazo)-2-naphthol (No. L19)

A reaction flask was loaded with ethanol (25 ml), sodium ethoxide (2.5 g), isopentyl nitrite (4.3 g), and 2-amino-3-methylpyridine (4 g), and they were mixed. The mixture was heated up to the reflux temperature of the solvent with stirring and stirred at the reflux temperature for 3 hours. Then, the heating was stopped and the mixture was cooled to room temperature with stirring. To this, 2-naphthol (3 g) dissolved in ethanol (5 ml) was dropwise added in 1.5 hours. The mixture was heated again and stirred at the reflux temperature for 4 hours. Then, the heating and stirring were stopped and the mixture was left to cool. The reaction mixture was filtered to remove insoluble components, and the filtrate was condensed. Water was added little by little to the residue for crystallization. The filtrated crystals were put into metanol (20 ml). This was stirred for 30 minutes, followed by recrystallization. The crystals were dried to give intended crystals (1.5 g).

Examples 1 to 27
Synthesis of Metal-containing Azo Compounds

Two azo compounds were selected from the above azo compounds (1) to (20) and reacted with a metal ion to obtain an intended metal-containing azo compound respectively.

In the synthesis of each metal-containing azo compound, a metal acetate was used and methanol or a methanol-dioxane mixed solvent was used as a solvent. In Examples 1 to 27, the synthesis of each compound was carried out by charging the azo compounds and the solvent into a reaction flask and stirring them followed by addition of the metal acetate, and then stirring at a reflux temperature of the solvent for 1 to 6 hours, and optionally purifying by means of recrystallization and so on. Reaction progress was almost quantitative and the intended product was obtained in an 80% yield in each example even when the product was purified.

It should be noted that there is a case where the finally obtained crystal contains a compound(s) in which the same two ligands are bonded to the metal as a by-product(s) in addition to the intended metal-containing azo compound of the present invention, however the presence of such by-product(s) does not greatly deteriorate the properties of the optical recording medium. Accordingly, when the crystal containing such by-product is used as it is to produce the optical recording medium of the present invention, the by-product does not affect the properties of the optical recording medium, and therefore it is not particularly necessary to remove the by-product.

In the following Tables 1 and 2, the kind of metal, the kinds of azo compound ligands bonded to the metal which are indicated by the above No. L○○ (○○ are numerals) and the mole ratio of the azo compounds when they were reacted with the metal ion (i.e. when charged) are shown for each metal-containing azo compound.

TABLE 1

| | Metal | Azo compound | Mole ratio | Decomposition temperature (° C.) | Optical constant (n/k) |
|---|---|---|---|---|---|
| Example 1 | Zn | L21/L26 | 2/1 | 340 | 2.4/0.03 |
| Example 2 | Cu | L21/L26 | 1/1 | 300 | 2.2/0.05 |
| Example 3 | Ni | L21/L26 | 1/1 | 340 | 2.2/0.06 |
| Example 4 | Zn | L21/L30 | 1/1 | 350 | 2.3/0.04 |
| Example 5 | Zn | L21/L30 | 2/1 | 350 | 2.3/0.02 |

TABLE 1-continued

| | Metal | Azo compound | Mole ratio | Decomposition temperature (° C.) | Optical constant (n/k) |
|---|---|---|---|---|---|
| Example 6 | Zn | L21/L30 | 1/2 | 350 | 2.4/0.05 |
| Example 7 | Zn | L21/L29 | 1/1 | 320 | 2.2/0.02 |
| Example 8 | Zn | L21/L08 | 1/1 | 340 | 2.3/0.04 |
| Example 9 | Zn | L57/L78 | 2/1 | 360 | 2.1/0.04 |
| Example 10 | Zn | L69/L70 | 1/1 | 305 | 2.2/0.04 |
| Example 11 | Zn | L56/L45 | 2/1 | 370 | 2.1/0.03 |
| Example 12 | Zn | L69/L21 | 1/1 | 300 | 2.3/0.04 |
| Example 13 | Zn | L69/L56 | 1/1 | 310 | 2.1/0.04 |
| Example 14 | Zn | L69/L56 | 1/2 | 320 | 2.2/0.03 |
| Example 15 | Zn | L70/L21 | 1/1 | 350 | 2.0/0.03 |
| Example 16 | Zn | L70/L56 | 1/1 | 360 | 2.2/0.03 |

TABLE 2

| | Metal | Azo compound | Mole ratio | Decomposition temperature (° C.) | Optical constant (n/k) |
|---|---|---|---|---|---|
| Example 17 | Ni | L140/L30 | 1/1 | 360 | 2.4/0.3 |
| Example 18 | Ni | L116/L30 | 1/1 | 320 | 2.4/0.09 |
| Example 19 | Ni | L132/L30 | 1/1 | 370 | 2.5/0.16 |
| Example 20 | Zn | L08/L30 | 1/1 | 370 | 2.4/0.11 |
| Example 21 | Ni | L08/L30 | 1/1 | 360 | 2.6/0.3 |
| Example 22 | Ni | L21/L30 | 1/1 | 370 | 2.5/0.11 |
| Example 23 | Ni | L21/L30 | 1/2 | 380 | 2.5/0.13 |
| Example 24 | Zn | L26/L70 | 1/1 | 360 | 2.4/0.04 |
| Example 25 | Zn | L26/L69 | 1/1 | 300 | 2.4/0.04 |
| Example 26 | Zn | L116/L30 | 1/1 | 310 | 2.4/0.05 |
| Example 27 | Zn | L19/L30 | 1/1 | 370 | 2.3/0.05 |

The structural formulae of metal-containing azo compounds each obtained in Examples 1 to 27 are shown below:

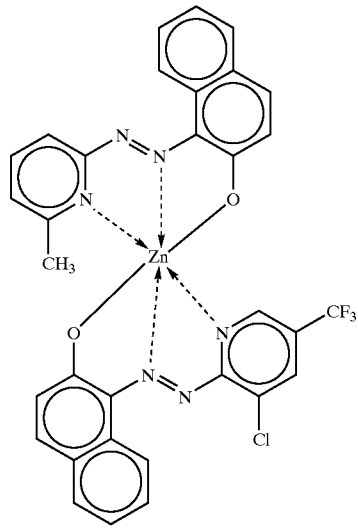

Example 1

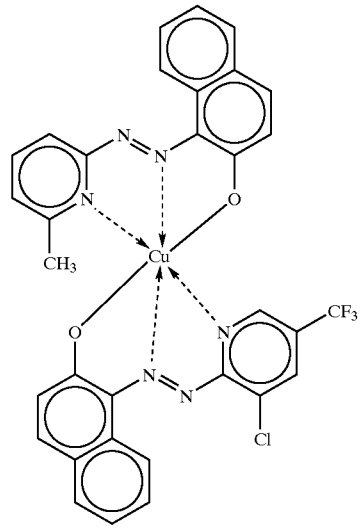

Example 2

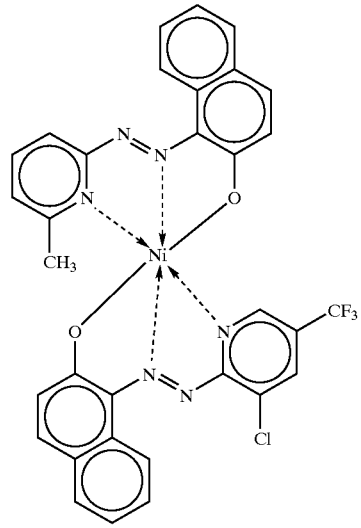

Example 3

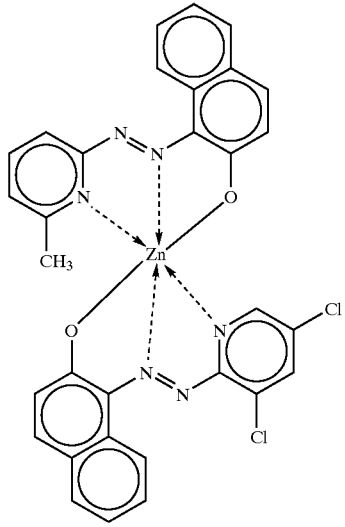

Examples 4, 5, 6

-continued
Example 7
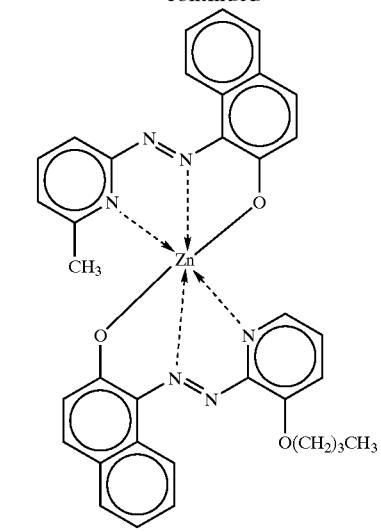
Example 8
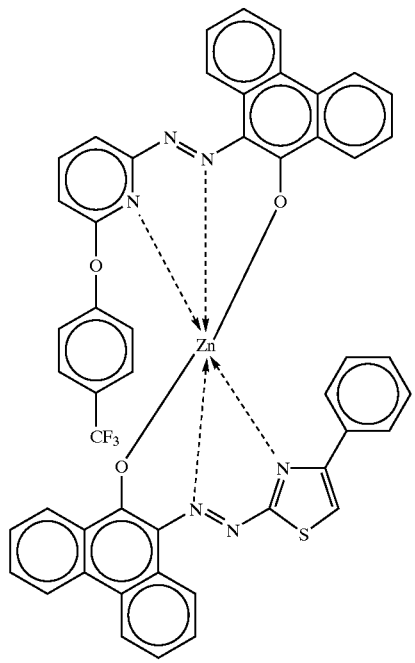
Example 9
Example 10
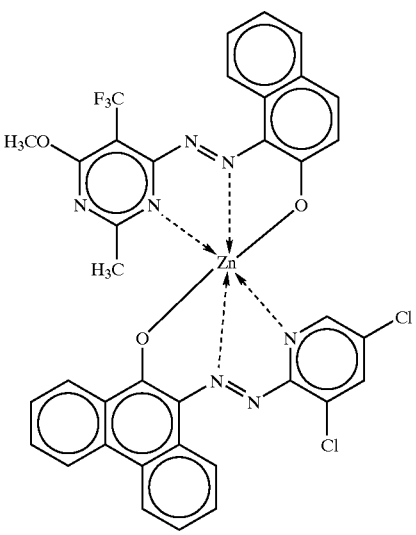
Example 11
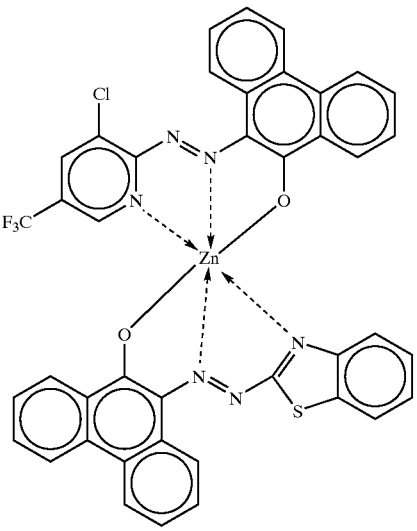
Example 12
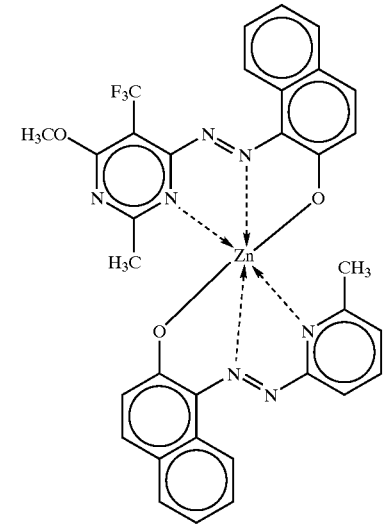

-continued
Examples 13, 14
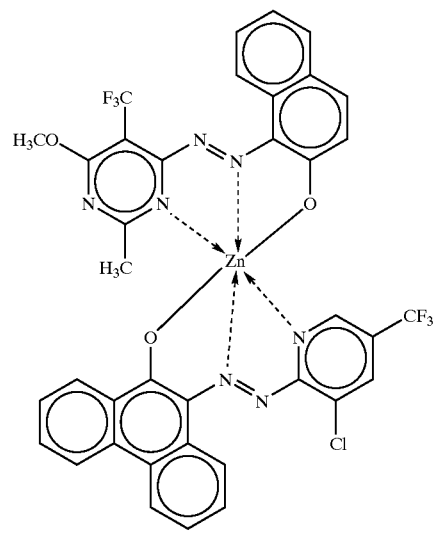
Example 15
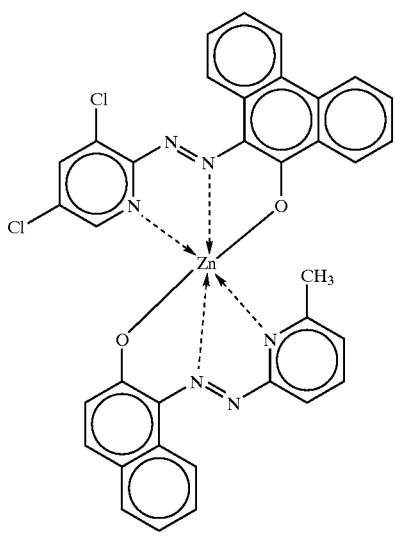
Example 16
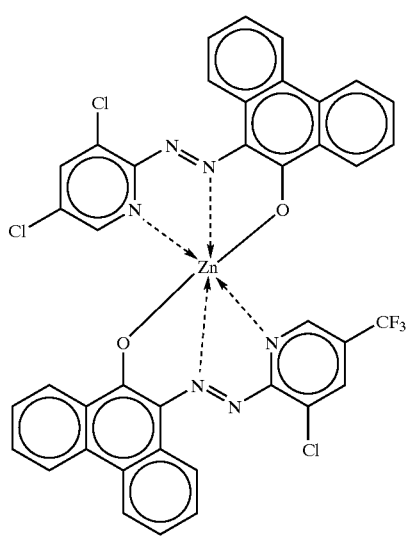
-continued
Example 17
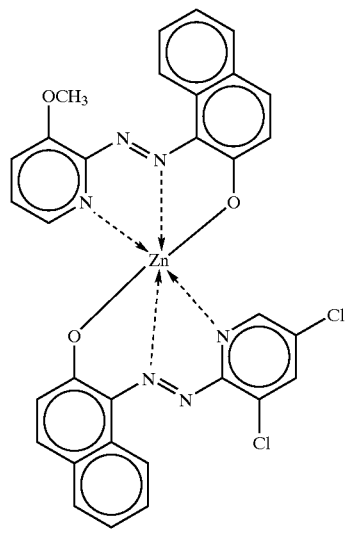
Example 18
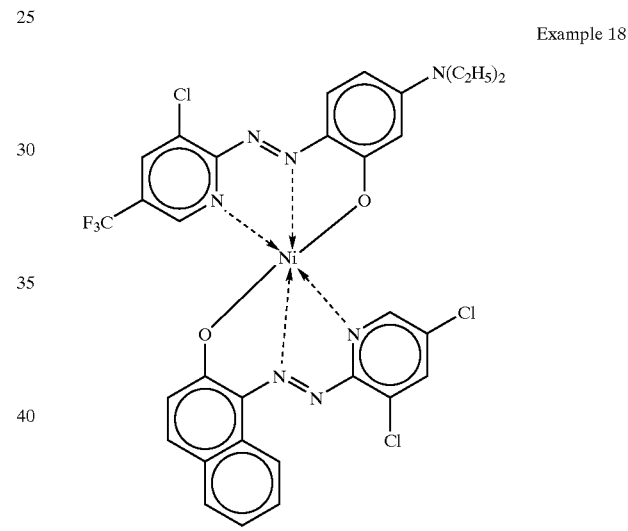
Example 19
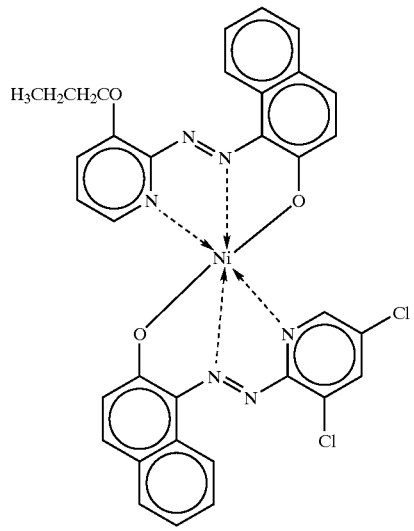

Example 20
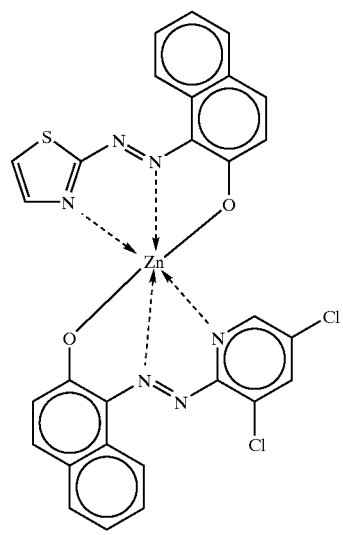
Example 24
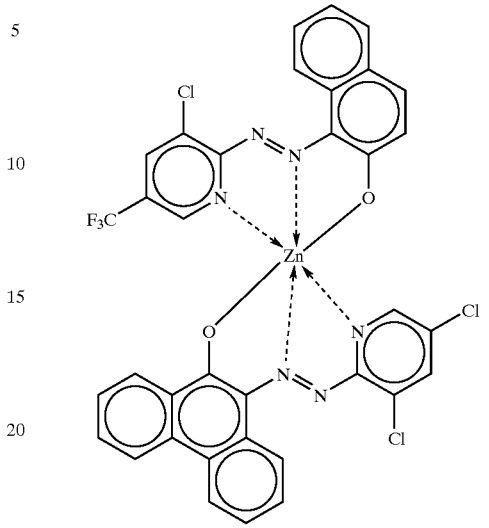
Example 21
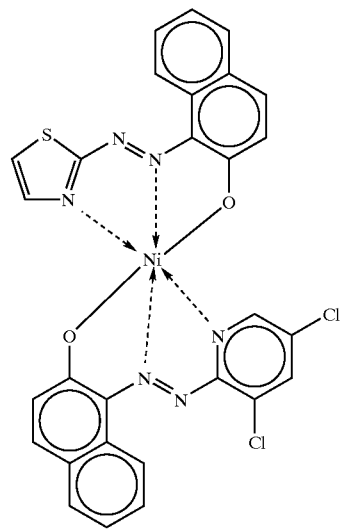
Example 25
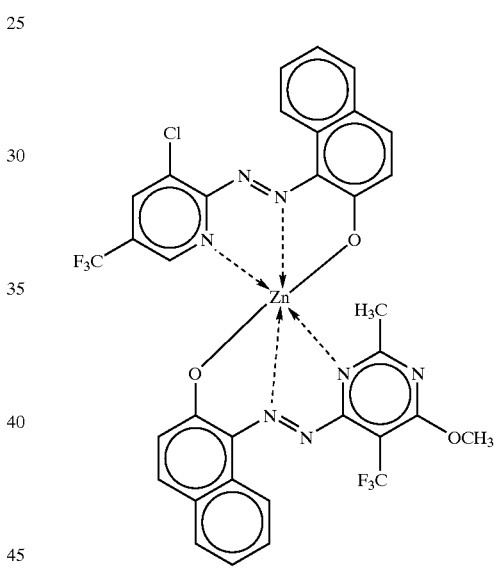
Examples 22, 23
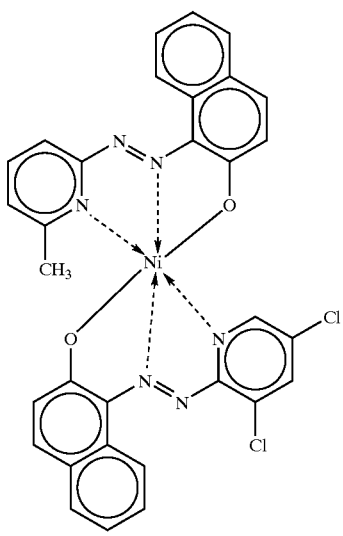
Example 26
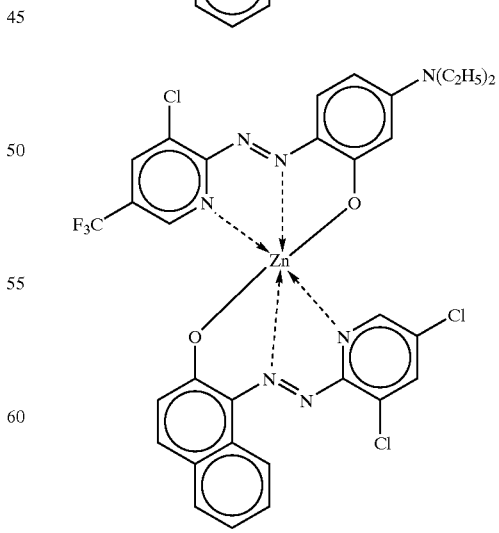

-continued

Example 27

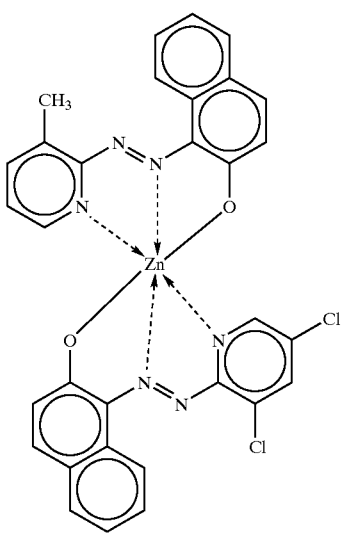

As to the compounds obtained in Examples 4, 15, 17, 19, 22 and 26, the infrared spectrums are shown in FIGS. 2 to 7.

Production of Optical Recording Medium

Optical recording media as shown in FIG. 1 were produced by forming a recording layer (2) by a vapor deposition method using each metal-containing azo compound. Here, a plate of polycarbonate having a diameter of 120 mm and a thickness of 0.6 mm was used as a substrate (1). On one surface, this substrate had a spiral groove (6) with a groove width of 0.27 μm, a track pitch of 0.74 μm, a value of 0.36 which was obtained by dividing the groove width by the track pitch and a value of 0.49 which was obtained by dividing a groove depth (herein 51 nm) by $\lambda/(4n)$. Further, a pressure employed in vapor deposition was $10^{-4}$ Torr and the heating temperatures of the metal-containing azo compounds were 200 to 400° C.

Here, a reflective layer (3) was formed to a thickness of 100 nm by sputtering gold. An ultraviolet-curable acrylic resin was laminated thereon as an adhesive layer (4) and a substrate (5) made of the same material and having the same thickness as the substrate (1) was laminated on the adhesive layer.

As to the optical recording media produced in this manner, power, output, and tracking stability were evaluated in unrecorded state. The results are shown in Tables 3 and 4.

TABLE 3

| | Power(mW)/ Linear velocity (m/s) | Output 3T/14T | Tracking stability |
|---|---|---|---|
| Example 1 | 11/3.5 | 140/600 | ○ |
| Example 2 | 10/3.5 | 80/400 | ○ |
| Example 3 | 11/3.5 | 110/430 | ○ |
| Example 4 | 11/3.5 | 150/500 | ○ |
| Example 5 | 12/3.5 | 100/480 | ○ |
| Example 6 | 11/3.5 | 90/500 | ○ |
| Example 7 | 12/3.5 | 80/480 | ○ |
| Example 8 | 12/3.5 | 90/450 | ○ |
| Example 9 | 12/3.5 | 80/380 | ○ |
| Example 10 | 12/3.5 | 120/450 | ○ |
| Example 11 | 12/3.5 | 100/470 | ○ |
| Example 12 | 12/3.5 | 90/470 | ○ |
| Example 13 | 12/3.5 | 100/500 | ○ |
| Example 14 | 12/3.5 | 100/500 | ○ |
| Example 15 | 12/3.5 | 100/460 | ○ |
| Example 16 | 12/3.5 | 100/500 | ○ |

TABLE 4

| | Power (mW)/ Linear velocity m/s | Output 3T/14T | Tracking stability |
|---|---|---|---|
| Example 17 | 9.4/3.5 | 46/214 | ○ |
| Example 18 | 11/3.5 | 78/360 | ○ |
| Example 19 | 9.0/3.5 | 48/240 | ○ |
| Example 20 | 9.5/3.5 | 61/290 | ○ |
| Example 21 | 8/3.5 | 36/180 | ○ |
| Example 22 | 9.5/3.5 | 84/420 | ○ |
| Example 23 | 8.5/3.5 | 54/252 | ○ |
| Example 24 | 9.5/3.5 | 72/444 | ○ |
| Example 25 | 9.5/3.5 | 72/408 | ○ |
| Example 26 | 10.5/3.5 | 84/432 | ○ |
| Example 27 | 10/3.5 | 78/360 | ○ |

From these results, it is seen that each of the optical recording media of which recording layer comprises the metal-containing azo compound in which two different azo compound ligands are bonding according to the present invention has good performance as a whole.

Industrial Applicability

The metal-containing azo compound of the present invention is one in which two different azo compound ligands are bonded to the metal. When the metal-containing azo compound is used in a recording layer of an optical recording medium, the characteristics of each azo compound ligand bonded to the metal, such as optical absorption and so on appear moderately. Accordingly, the optical recording medium of which recording layer is formed using the metal-containing azo compound of the present invention has particularly excellent performance as a whole. Further, according to the present invention, proper selection of the combination of the azo compound ligands makes it possible to provide an optical recording medium having many various properties.

What is claimed is:

1. An optical recording medium having a recording layer formed on a substrate, the recording layer allowing writing and/or reading information by a laser beam, in which the recording layer comprises a metal-containing azo compound represented by at least one formula which is selected from the following general formulae (a1), (a2), (a3) and (a4):

formula (a1)

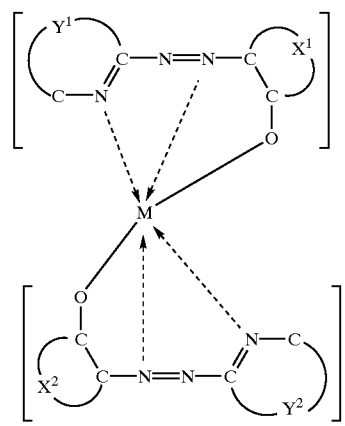

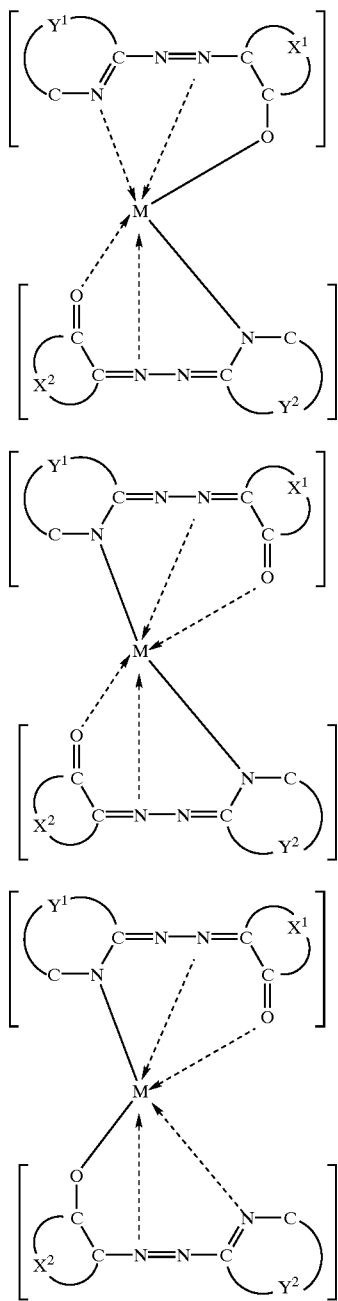

formula (a2)

formula (a3)

formula (a4)

wherein M(II) is a bivalent metal, each of $X^1$ and $X^2$ is a substituted or non-substituted residue that forms a monocyclic or polycyclic aromatic ring together with carbon atoms that are adjacent thereto at its both ends, each of $Y^1$ and $Y^2$ is a substituted or non-substituted residue that forms a nitrogen-containing aromatic heterocycle together with a nitrogen atom and carbon atoms that are adjacent thereto at its both ends, and a substituent when present in the residue is independently selected from the group consisting of a halogen atom, a substituted and non-substituted alkyl group, a substituted and non-substituted alkoxyl group, a substituted and non-substituted alkylthio group, a substituted and non-substituted aryl group, a substituted and non-substituted aryloxyl group, a substituted and non-substituted arylthio group, a nitro group, and a substituted and non-substituted amino group, and one residue is different from the other in at least one of a combination of $X^1$ and $X^2$ and a combination of $Y^1$ and $Y^2$.

2. The optical recording medium according to claim 1 in which, when one or more residues selected from $X^1$, $X^2$, $Y^1$ and $Y^2$ have a substituent(s), the carbon number of the substituent(s) is 1 to 9.

3. The optical recording medium according to claim 1 in which $X^1$ and/or $X^2$ forms a phenanthrene ring, a naphthalene ring, or a benzene ring together with the adjacent carbon atoms.

4. The optical recording medium according to claim 1 in which $Y^1$ and/or $Y^2$ forms a pyridyl group, a pyrimidinyl group, a pyrazinyl group, a triazinyl group, a thiazolyl group or a benzothiazolyl group together with the nitrogen atom and the carbon atoms adjacent thereto.

5. The optical recording medium according to claim 1 in which substituents $R^1$ and $R^2$ which are bonded respectively to carbon atoms adjacent to the residues $Y^1$ and $Y^2$ respectively are included in the general formulae (a1), (a2), (a3) and (a4), and $R^1$ and $R^2$ are each selected from the group consisting of a hydrogen atom, a substituted and non-substituted alkyl group, a substituted and non-substituted alkoxyl group, a substituted and non-substituted alkylthio group, a substituted and non-substituted aryl group, a substituted and non-substituted aryloxyl group, and a substituted and non-substituted arylthio group, and in at least one of the combination of the residues $X^1$ and $X^2$, the combination of the residues $Y^1$ and $Y^2$, and a combination of substituents $R^1$ and $R^2$, the residues or the substituents are different from each other.

6. The optical recording medium according to claim 5 in which $R^1$ and/or $R^2$ is selected from the group consisting of a substituted and non-substituted alkyl group having 1 to 9 carbon atoms, a substituted and non-substituted alkoxyl group having 1 to 9 carbon atoms, a substituted and non-substituted alkylthio group having 1 to 9 carbon atoms, a substituted and non-substituted aryl group having 6 to 9 carbon atoms, a substituted and non-substituted aryloxyl group having 6 to 9 carbon atoms, and a substituted and non-substituted arylthio group having 6 to 9 carbon atoms.

7. The optical recording medium according to claim 5 in which $R^1$ and/or $R^2$ is selected from the group consisting of a methyl group, an ethyl group, a butyl group, a phenyl group, a methoxyl group, an ethoxyl group, a butoxyl group, a phenoxyl group, a methylthio group, an ethylthio group, a butylthio group, and a phenylthio group; or any one of the these groups of which at least one hydrogen atom is substituted with a halogen atom.

8. The optical recording medium according to claim 5 in which $R^1$ and/or $R^2$ is a hydrogen atom.

9. The optical recording medium according to claim 5 in which $Y^1$ and/or $Y^2$ forms a pyridyl group, a pyrimidinyl group, a pyrazinyl group, a triazinyl group, or a thiazolyl group together with the nitrogen atom and the carbon atoms adjacent thereto.

10. The optical recording medium according to claim 5 in which the substrate has a spiral groove with the groove width ($\mu$m), the groove depth (nm), and the track pitch ($\mu$m) which satisfy the following relation:

0.25≦groove width/track pitch≦0.45

0.2λ/(4n)≦groove depth≦0.8λ/(4n)

wherein λ is the wavelength (nm) of the laser beam used for recording and "n" is the refractive index of the substrate.

11. The optical recording medium according to claim 1 in which the substrate has a spiral groove with the groove width ($\mu$m), the groove depth (nm), and the track pitch ($\mu$m) which satisfy the following relation:

0.25≦groove width/track pitch≦0.45

0.2λ/(4n)≦groove depth≦0.8λ/(4n)

wherein λ is the wavelength (nm) of the laser beam used for recording and "n" is the refractive index of the substrate.

12. The optical recording medium according to claim 1 in which the recording layer is formed by a wet process.

13. The optical recording medium according to claim 1 in which the recording layer is formed by a vapor deposition method.

14. The optical recording medium according to claim 11 in which the recording layer is formed by a vapor deposition method.

15. A metal-containing azo compound represented by at least one formula which is selected from the following general formulae (a1), (a2), (a3) and (a4):

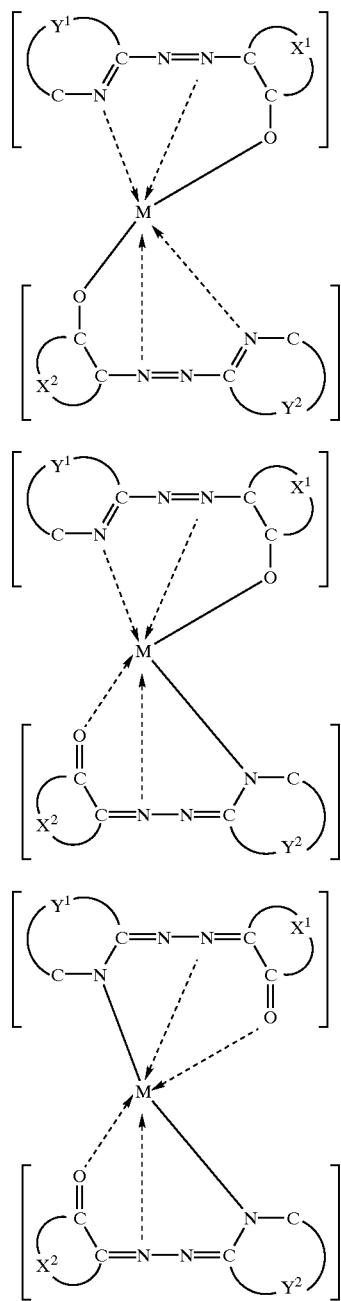

formula (a1)

formula (a2)

formula (a3)

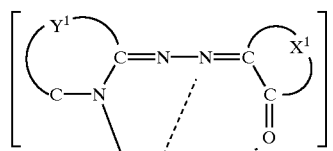

formula (a4)

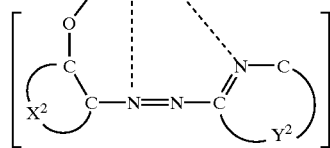

wherein M(II) is a bivalent metal, each of $X^1$ and $X^2$ is a substituted or non-substituted residue that forms a monocyclic or polycyclic aromatic ring together with carbon atoms that are adjacent thereto at its both ends, each of $Y^1$ and $Y^2$ is a substituted or non-substituted residue that forms a nitrogen-containing aromatic heterocycle together with a nitrogen atom and carbon atoms that are adjacent thereto at its both ends, and a substituent when present in the residue is independently selected from the group consisting of a halogen atom, a substituted and non-substituted alkyl group, a substituted and non-substituted alkoxyl group, a substituted and non-substituted alkylthio group, a substituted and non-substituted aryl group, a substituted and non-substituted aryloxyl group, a substituted and non-substituted arylthio group, a nitro group, and a substituted and non-substituted amino group, and one residue is different from the other in at least one of a combination of $X^1$ and $X^2$ and a combination of $Y^1$ and $Y^2$;

the compound includes substituents $R^1$ and $R^2$ which are bonded respectively to carbon atoms adjacent to the residues $Y^1$ and $Y^2$ respectively;

$R^1$ and $R^2$ are each selected from the group consisting of a hydrogen atom, a substituted and non-substituted alkyl group having 1 to 9 carbon atoms, a substituted and non-substituted alkoxyl group having 1 to 9 carbon atoms, a substituted and non-substituted alkylthio group having 1 to 9 carbon atoms, a substituted and non-substituted aryl group having 6 to 9 carbon atoms, a substituted and non-substituted aryloxyl group having 6 to 9 carbon atoms, and a substituted and non-substituted arylthio group having 6 to 9 carbon atoms;

when one of $R^1$ and $R^2$ is a hydrogen atom, the other is not a hydrogen atom; and at least one of a combination of the residues $X^1$ and $X^2$, a combination of the residues $Y^1$ and $Y^2$, and a combination of substituents $R^1$ and $R^2$, the residues or the substituents are different from each other.

16. The metal-containing azo compound according to claim 15 in which, when one or more residues selected from $X^1, X^2, Y^1$ and $Y^2$ have a substituent(s), the carbon number of the substituent(s) is 1 to 9.

17. The metal-containing azo compound according to claim 15 in which $X^1$ and/or $X^2$ forms a phenanthrene ring, a naphthalene ring, or a benzene ring together with the adjacent carbon atoms.

18. The metal-containing azo compound according to claim 15 in which $R^1$ and/or $R^2$ is selected from the group consisting of a methyl group, an ethyl group, a butyl group, a phenyl group, a methoxyl group, an ethoxyl group, a butoxyl group, a phenoxyl group, a methylthio group, an ethylthio group, a butylthio group, and a phenylthio group; or any one of the these groups of which at least one hydrogen atom is substituted with a halogen atom.

19. The metal-containing azo compound according to claim 15 in which $Y^1$ and/or $Y^2$ forms a pyridyl group a pyrimidinyl group, a pyrazinyl group, a triazinyl group, a thiazolyl group together with the nitrogen atom and the carbon atoms adjacent thereto.

* * * * *